US012565684B2

(12) United States Patent
Bakaher

(10) Patent No.: US 12,565,684 B2
(45) Date of Patent: Mar. 3, 2026

(54) METHOD FOR CLASSIFYING PLANT MATERIAL

(71) Applicant: PHILIP MORRIS PRODUCTS S.A., Neuchatel (CH)

(72) Inventor: Nicolas Jean-Pierre Olivier Bakaher, Villers-leLac (FR)

(73) Assignee: Philip Morris Products S.A., Neuchatel (CH)

( * ) Notice: Subject to any disclaimer, the term of this patent is extended or adjusted under 35 U.S.C. 154(b) by 607 days.

(21) Appl. No.: 17/055,211

(22) PCT Filed: May 23, 2019

(86) PCT No.: PCT/EP2019/063311
§ 371 (c)(1),
(2) Date: Nov. 13, 2020

(87) PCT Pub. No.: WO2019/224298
PCT Pub. Date: Nov. 28, 2019

(65) Prior Publication Data
US 2021/0222262 A1 Jul. 22, 2021

(30) Foreign Application Priority Data
May 25, 2018 (EP) ...................................... 18305638

(51) Int. Cl.
*C12Q 1/6895* (2018.01)
(52) U.S. Cl.
CPC ....... *C12Q 1/6895* (2013.01); *C12Q 2600/13* (2013.01)
(58) Field of Classification Search
CPC ........................... C12Q 1/6895; C12Q 2600/13
See application file for complete search history.

(56) References Cited

U.S. PATENT DOCUMENTS

2013/0167270 A1* 6/2013 Sala ..................... C12Q 1/6895
800/320.2

FOREIGN PATENT DOCUMENTS

| | | |
|---|---|---|
| CN | 102199655 | 9/2011 |
| GB | 2208346 | 3/1989 |
| WO | WO 02/077277 | 10/2002 |
| WO | WO 2006/040448 | 4/2006 |
| WO | WO 2013/080045 | 6/2013 |

OTHER PUBLICATIONS

Taberlet et al., "Universal Primers for amplification of three non-coding regions of chloroplast DNA", Plant Molecular Biology, 1991. vol. 17. 1105-1109. (Year: 1991).*
Yukawa, M. et al., "The chloroplast genome of Nicotiana sylvestris and Nicotiana tomentosiformis: complete sequencing confirms that the Nicotiana sylvestris progenitor is the maternal genome donor of Nicotiana tabacum", Mol. Genet. Genomics. 2006. vol. 275. (4), 367-373. (Year: 2006).*
Van der Hulst et al.,"Nuclear-Cytoplasmic male-sterility in diploid dandelions", Heredity. 2004., vol. 93: 43-50 (Year: 2004).*
Hakansson et al., "Variant mitochondrial protein and DNA patterns associated with cytoplasmic male-sterile lines of Nicotiana", Theor Appl Genet.1988., vol. 76: 431-437 (Year: 1988).*
Tezuka et al. "Hybrid Lethality in Genus *Nicotiana*", Ann Bot. 2010., vol. 102(2):267-276 (Year: 2010).*
Storchova et al., "The architecture of the chloroplast psbA-trnH non-coding region in angiosperms". Pl Syst Evol., 2007, vol. 268: 235-256 (Year: 2007).*
Yukawa et al. "The chloroplast genome of Nicotiana sylvestris and Nicotiana tomentosiformis : complete sequencing confirms that the Nicotiana sylvestris progenitor is the maternal genome donor of Nicotiana tabacum" 2006. Mol. Gen Genomics, vol. 275: 367-373 (Year: 2006).*
Taberlet et al."Power and limitations of the chloroplast trnL (UAA) intron for plant DNA barcoding" Nucleic Acids Research, 2007, vol. 35, No. 3:1-8 (Year: 2007).*
Extended European Search Report for Application No. 18305638.1 dated Nov. 7, 2018 (5 pages).
PCT International Search Report and Written Opinion for PCT/EP2019/063311 dated Jun. 29, 2019 (9 pages).
Office Action issued in Korea for Application No. 10-2020-7037089 dated Aug. 29, 2024 (11 pages). English translation included.
Jo et al., "Complete Sequencing and Comparative Analyses of the Pepper (*Capsicus annuum* L.) Plastome Revealed High Frequency of Tandem Repeats and Large Insertion/Deletions on Pepper Plastome", *Plant Cell Rep* (2011) 30:217-229.
Wernsman EA, Rufty RC (1987) Tobacco. In: Fehr W (ed) Principles of cultivar development, vol. 2. Macmillan Publ, New York, pp. 669-698.

(Continued)

*Primary Examiner* — Neil P Hammell
*Assistant Examiner* — Kelly Nichet Hassell
(74) *Attorney, Agent, or Firm* — Mueting Raasch Group

(57) ABSTRACT

A method for classifying a batch of plant material as either being contaminated or non-contaminated includes: (i) providing a sample of polynucleotide from the batch; (ii) contacting the sample with one or more amplification primers to amplify a polynucleotide sequence associated with sterility; (iii) performing an in vitro polynucleotide amplification reaction on the sample to generate one or more amplification products; (iv) determining the size or sequence of the amplification product(s); and (v) comparing the size or sequence of the amplification product(s) with known amplification product(s) from known genetic sources of sterility. If the genetic source of sterility determined in (v) corresponds to the expected genetic source of sterility of the batch then said batch is considered non-contaminated; or wherein if the genetic source of sterility determined in (v) does not correspond to the expected genetic source of sterility of the batch then said batch is considered contaminated.

18 Claims, No Drawings
Specification includes a Sequence Listing.

(56) References Cited

OTHER PUBLICATIONS

Genbank Accession Number: National Center for Biotechnology Information, National Library of Medicine, National Institutes of Health, GenBank Locus FJ493313, Accession No. FJ493313, "Nicotiana Tabacum Photosystem II Protein D1 (PsbA) Gene, Partial CDs; psbA-trnH Intergenic Spacer, Complete Sequence; and tRNA-His (trnH) Gene, Partial Sequence; Chloroplast". Retrieved from the Internet: https://www.ncbi.nlm.nih.gov/nucleotide/218203173?report= genbank&log$=nuclalign&blast_rank=3&RID=VCR8E770014.

* cited by examiner

METHOD FOR CLASSIFYING PLANT MATERIAL

This application is a U.S. National Stage Application of International Application No. PCT/EP2019/063311 filed May 23, 2019, which was published in English on Nov. 28, 2019 as International Publication No. WO 2019/224298 A1. International Application No. PCT/EP2019/063311 claims priority to European Application No. 18305638.1 filed May 25, 2018.

FIELD OF THE INVENTION

The present disclosure relates in general to classifying a batch of plant material as either being contaminated or non-contaminated. The classification is based on the analysis of one or more polynucleotide sequences associated with sterility. By carrying out the methods described herein it is possible to determine if the batch or lot of plant material is contaminated or non-contaminated to ensure the quality or the integrity of the plant material. In particular, the disclosure makes it possible to readily determine if a batch of plant material has been adulterated.

BACKGROUND

Commercially prepared tobacco seeds are sold to farmers for them to grow tobacco plants. To ensure the quality of the tobacco that is produced it is generally desirable for the producer of the seed to be able to test the tobacco plants or the tobacco product derived therefrom to check that it is derived from the tobacco seeds provided to the farmer. It is also desirable for the seed producers to be able to check that the tobacco plants or the tobacco product being sold has not been contaminated or adulterated with tobacco from other seed sources and is obtained wholly from the supplied seed. This helps to ensure the quality of the tobacco plants or the tobacco product derived therefrom. For example, tobacco batches or lots that contain tobacco derived from anything other than the commercially prepared tobacco seeds that have been sold to farmers may be of inferior quality and may have to be discarded.

There is a need in the art for a test that can be used to check the quality or adulteration of plant material—such as tobacco material—or a product derived therefrom. In particular, there is a need in the art for a simplified method that can be used at any stage of plant product production that is amenable to high throughput analysis.

SUMMARY OF THE INVENTION

Commercially prepared tobacco seeds are often sold in non-fertile form. Cytoplasmic male sterility (CMS) is the main way of producing non-fertile tobacco plants for commercial use and is a common genetic source of sterility. CMS is produced by transferring the *Nicotiana tabacum* nuclear genome into the cytoplasm of species of the same genus via backcrosses. Commercially, the most abundant sources of sterility are derived from the *Nicotiana suaveolens* cytoplasm or the *Nicotiana glauca* cytoplasm. The present disclosure provides methods that make it possible to readily differentiate fertile plant material from sterile plant material through the analysis of at least one (or only one) polynucleotide sequence that is polymorphic between plant species or varieties that are to be subjected to analysis-such as at least *Nicotiana tabacum, Nicotiana suaveolens* and *Nicotiana glauca*. If the results of the analysis indicate that the fertility of the plant material is not as expected then this is indicative that the plant material has been contaminated or is adulterated and is, for example, non-conforming. This differentiation can be achieved as certain polynucleotide sequences associated with sterility in certain plant species have different polymorphisms (for example, deletions or additions) therein such that differences in the size or sequence of each the amplified polynucleotide sequences allows for the identification of the species from which the polynucleotide sequences is derived. In certain embodiments, it is possible to differentiate *Nicotiana tabacum* cytoplasm (fertile material) from *Nicotiana suaveolens* cytoplasm (sterile material) or *Nicotiana glauca* cytoplasm (sterile material). According to the results of this analysis, if the genetic source of sterility corresponds to the expected genetic source of sterility of the batch of plant material being tested then the batch of plant material is considered to be non-contaminated or non-adulterated (for example, conforming) as there is no indication that the plant material has been contaminated with plant material containing a different genetic source of sterility. If the genetic source of sterility does not correspond to the expected genetic source of sterility of the batch of plant material then the batch of plant material is considered to be contaminated or adulterated (for example, non-conforming) as there is an indication that the plant material has been contaminated or adulterated with plant material containing a different genetic source of sterility. In some instances, the genetic source of sterility may not correspond to the expected genetic source of sterility of the batch of plant material because a genetic source of sterility is not detectable. In the event that the batch of plant material is found to be non-contaminated (for example, conforming) it can be expected that the plant material is free from contamination or adulteration and that the plant material derived therefrom will be of the expected quality or purity. In the event that the batch of plant material is found to be contaminated or adulterated (for example, non-conforming) then it can be expected that the plant material has been contaminated with other plant material and that the plant material derived therefrom will not be of the expected quality or purity. In this case, the plant material may need to be discarded or destroyed as the quality or purity thereof cannot be assured.

The present invention can be used to determine fertility status in sterile hybrids-such as sterile tobacco hybrids. Accordingly, the present invention can be applied to classifying sterile hybrids-such as sterile hybrid crops in farmer fields.

In one aspect, there is described a method for classifying a batch of plant material as either being contaminated or non-contaminated comprising: (i) providing a sample of polynucleotide from the batch of plant material; (ii) contacting the sample of polynucleotide with one or more amplification primers to amplify a target polynucleotide sequence associated with sterility; (iii) performing an in vitro polynucleotide amplification reaction on the sample to generate one or more amplification products; (iv) determining the size or sequence of the amplification product(s); and (v) based on the size or sequence of the amplification product(s) determined in step (iv) comparing the size or sequence of the amplification product(s) with the size or sequence of known amplification product(s) from known genetic sources of sterility; wherein if the genetic source of sterility determined in step (v) corresponds to the expected genetic source of sterility of the batch of plant material then said batch of plant material is considered to be non-contaminated; or wherein if the genetic source of sterility determined in step (v) does not correspond to the expected genetic source of sterility of the batch of plant material then said batch of plant material is considered to be contaminated.

Suitably, the target polynucleotide sequence associated with sterility is a polynucleotide sequence associated with cytoplasmic male sterility.

Suitably, the presence of a polynucleotide sequence associated with sterility from *Nicotiana suaveolens, Nicotiana glauca, Nicotiana bigelovii, Nicotiana plumbaginifolia, Nicotiana megalosiphon* or *Nicotiana undulata* is indicative that the plant material is sterile; suitably, wherein a polynucleotide sequence associated with sterility from *Nicotiana suaveolens* or *Nicotiana glauca* is indicative that the plant material is sterile.

Suitably, the target polynucleotide sequence associated with sterility is from the chloroplast or mitochondria.

Suitably, the target polynucleotide sequence associated with sterility is an intergenic spacer, suitably, wherein the intergenic spacer is a chloroplastic or mitochondrial intergenic spacer. Suitably, the chloroplastic intergenic spacer is selected from the group consisting of a trnH-psbA chloroplastic intergenic spacer, a trnL-trnF chloroplastic intergenic spacer, a ndhC-trnV chloroplastic intergenic spacer, a petA-psbJ chloroplastic intergenic spacer, a petN-psbM chloroplastic intergenic spacer, a psbE-petL chloroplastic intergenic spacer, a psbM-trnD chloroplastic intergenic spacer, a rbc1-accD chloroplastic intergenic spacer, a rpoD-trnC chloroplastic intergenic spacer, a rps16-trnQ chloroplastic intergenic spacer, a trnS-trnG chloroplastic intergenic spacer, a trnT-psbD chloroplastic intergenic spacer, a trnW-psaJ chloroplastic intergenic spacer, or a ycf1 chloroplastic intergenic spacer or a combination of two or more thereof, suitably, wherein the trnH-psbA chloroplastic intergenic spacer comprises or consists of the sequence set forth in SEQ ID NO: 1 or the trnL-trnF chloroplastic intergenic spacer comprises or consists of the sequence set forth in SEQ ID NO: 5.

Suitably, the batch of plant material to be classified is *Nicotiana tabacum* plant material. Suitably, the batch of plant material to be classified is *Nicotiana tabacum* plant material and wherein the expected genetic source of sterility is cytoplasmic male sterility from *Nicotiana suaveolens, Nicotiana glauca, Nicotiana bigelovii, Nicotiana plumbaginifolia, Nicotiana megalosiphon* or *Nicotiana undulata,* suitably, *Nicotiana suaveolens* or *Nicotiana glauca.*

Suitably, the batch of plant material to be classified is *Nicotiana tabacum* plant material and wherein the expected genetic source of sterility is cytoplasmic male sterility from *Nicotiana suaveolens,* and wherein if the genetic source of sterility determined in step (v) corresponds to cytoplasmic male sterility from *Nicotiana suaveolens* then said batch of plant material is considered to be non-contaminated; or wherein if the genetic source of sterility determined in step (v) does not correspond to cytoplasmic male sterility from *Nicotiana suaveolens* then said batch of plant material is considered to be contaminated.

Suitably, the batch of plant material for checking is *Nicotiana tabacum* plant material and wherein the expected genetic source of sterility is cytoplasmic male sterility from *Nicotiana glauca,* and wherein if the genetic source of sterility determined in step (v) corresponds to cytoplasmic male sterility from *Nicotiana glauca* then said batch of plant material is considered to be non-contaminated; or wherein if the genetic source of sterility determined in step (v) does not correspond to cytoplasmic male sterility from *Nicotiana glauca* then said batch of plant material is considered to be contaminated.

Suitably, the plant material is selected from the group consisting of seedlings, seeds, plants, parts of plants, harvested plant material, cured plant material or a combination of two or more thereof.

Suitably, the size of the amplification product is determined using gel electrophoresis, suitably, agarose gel electrophoresis or two dimensional gel electrophoresis or capillary electrophoresis; and/or wherein the sequence of the amplification product is determined using polynucleotide sequencing.

There is also disclosed a method for classifying a batch of plant material plant material as either being contaminated or non-contaminated comprising the use of one or more amplification primers specific for a polynucleotide sequence associated with sterility.

There is also disclosed the use of two or more amplification primers specific for a polynucleotide sequence associated with sterility for classifying a batch of plant material as either being contaminated or non-contaminated.

Suitably, the plant material is sterile hybrid plant material-such as sterile hybrid tobacco material.

Some Advantages

Advantageously, the present invention provides for a conformity or quality check at any stage of the tobacco production process, including on polynucleotide extracted from seeds or seedlings before transplanting in the field; on polynucleotide extracted from plants growing in the field; and/or on polynucleotide extracted from harvested material in a curing barn or at the buying station.

The target polynucleotide sequences-such as the intergenic spacers-associated with sterility have a different sequence in each of, for example, *Nicotiana tabacum, Nicotiana suaveolens* and *Nicotiana glauca* and this difference in sequence can be exploited to create a simple test to differentiate *Nicotiana tabacum* cytoplasm (fertile material) from *Nicotiana tabacum* cytoplasm (sterile material), *Nicotiana suaveolens* cytoplasm (sterile material) or *Nicotiana glauca* cytoplasm (sterile material). Based on the results of this analysis, it can be readily determined if a batch or lot of plant material is contaminated or adulterated or non-contaminated.

The method described herein does not require the use of a restriction enzyme digestion step for differentiating the amplification product(s). This can make the method faster and simpler. Furthermore, the method described herein is readily amenable to high throughput analysis using, for example, capillary electrophoresis.

Advantageously, short polynucleotide fragments can be amplified such that plant material containing degraded polynucleotides can be analysed as polynucleotides are often fragmented into short pieces in processed plant material-such as cured plant material. Suitably, the short polynucleotide fragments are 500 base pairs or less.

DETAILED DESCRIPTION

Section headings as used in this disclosure are for organisation purposes and are not intended to be limiting.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures.

The singular forms "a," "and" and "the" include plural references unless the context clearly dictates otherwise.

The term "and/or" means (a) or (b) or both (a) and (b).

The present disclosure contemplates other embodiments "comprising," "consisting of" and "consisting essentially of" the embodiments or elements presented herein, whether explicitly set forth or not.

An "amplification primer" is an oligonucleotide that is used for the amplification of a target polynucleotide sequence-such as an intergenic spacer associated with sterility, for example, a chloroplastic intergenic spacer associated with sterility. Accordingly, the amplification primer(s) targets, in certain embodiments, the chloroplast polynucleotide (for example, DNA) in an intergenic spacer region between certain genes. In general, this is achieved by extension of the oligonucleotide after hybridization to the target polynucleotide sequence. At least a portion of the amplification primer will hybridise to the complementary target polynucleotide sequence. This portion is referred to as the target binding sequence and it determines the target-specificity of the primer.

"Complementary" refers to Watson-Crick (for example, A-T/U and C-G) or Hoogsteen base pairing between nucleotides or nucleotide analogs. "Complementarity" refers to a property shared between two polynucleotides, such that when they are aligned antiparallel to each other, the nucleotide bases at each position will be complementary.

The term "expected genetic source of sterility" refers to the genetic source of sterility that the batch or lot of plant material is expected to have prior to carrying out the method or analysis described herein. This will normally be known in advance because prepared tobacco material-such as seeds or seedlings—are often sold in non-fertile form and the genetic source of this sterility will be known. For example, in Burley tobacco geographical areas, the CMS standard tends to be a *Nicotiana suaveolens* source of CMS. In flue-cured geographical areas, it tends to be a *Nicotiana glauca* source of CMS. In oriental geographical areas, it tends to be fertile *Nicotiana tabacum* such that a source of sterility is not used. Thus, in some instances, the tobacco seeds or seedlings are sold in fertile form in which case a genetic source of sterility will be absent when sold in this fertile form. The size or sequence of amplification products obtained or obtainable from these known genetic sources of sterility will also be known, which is exploited as described herein.

The terms "homology" or "similarity" refer to the degree of sequence similarity between two polynucleotides compared by sequence alignment. The degree of homology between two discrete polynucleotides being compared is a function of the number of identical, or matching, nucleotides at comparable positions.

"Identical" or "identity" in the context of two or more polynucleotides means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be determined manually or by using a computer sequence algorithm such as ClustalW, ClustalX, BLAST, FASTA or Smith-Waterman. The popular multiple alignment program ClustalW (Polynucleotides Research (1994) 22, 4673-4680; Polynucleotides Research (1997), 24, 4876-4882) is a suitable way for generating multiple alignments of polynucleotides. Suitable parameters for ClustalW maybe as follows: For polynucleotide alignments: Gap Open Penalty=15.0, Gap Extension Penalty=6.66, and Matrix=Identity. For DNA and Protein alignments: ENDGAP=−1, and GAPDIST=4. Those skilled in the art will be aware that it may be necessary to vary these and other parameters for optimal sequence alignment. Suitably, calculation of percentage identities is then calculated from such an alignment as (N/T), where N is the number of positions at which the sequences share an identical residue, and T is the total number of positions compared including gaps but excluding overhangs.

The terms "isolated" or "purified" refer to material that is substantially or essentially free from components that normally accompany it as found in its native state. Purity and homogeneity are typically determined using analytical chemistry techniques such as polyacrylamide gel electrophoresis or high performance liquid chromatography. The term "purified" as used herein denotes that a polynucleotide gives rise to essentially one band in an electrophoretic gel. Particularly, it means that the polynucleotide is at least 85% pure, more preferably at least 95% pure, and most preferably at least 99% pure. Isolated polynucleotides may be purified from a host cell in which they naturally occur. Conventional polynucleotide purification methods known to skilled artisans may be used to obtain isolated polynucleotides. The term also embraces recombinant polynucleotides and chemically synthesized polynucleotides.

"Oligonucleotide" or "polynucleotide" means at least two nucleotides covalently linked together. The depiction of a single strand also defines the sequence of the complementary strand. Thus, a polynucleotide also encompasses the complementary strand of a depicted single strand. Many variants of a polynucleotide may be used for the same purpose as a given polynucleotide. Thus, a polynucleotide also encompasses substantially identical polynucleotides and complements thereof. A single strand provides a probe that may hybridize to a given sequence under stringent hybridization conditions. Thus, a polynucleotide also encompasses a probe that hybridizes under stringent hybridization conditions. Polynucleotides may be single stranded or double stranded, or may contain portions of both double stranded and single stranded sequence. The polynucleotide may be DNA, both genomic and cDNA, RNA, or a hybrid, where the polynucleotide may contain combinations of deoxyribo- and ribo-nucleotides, and combinations of bases including uracil, adenine, thymine, cytosine, guanine, inosine, xanthine hypoxanthine, isocytosine and isoguanine.

Polynucleotides may be obtained by chemical synthesis methods or by recombinant methods.

The specificity of single-stranded DNA to hybridize complementary fragments is determined by the "stringency" of the reaction conditions (Sambrook et al., Molecular Cloning and Laboratory Manual, Second Ed., Cold Spring Harbor (1989)). Hybridization stringency increases as the propensity to form DNA duplexes decreases. In polynucleotide hybridization reactions, the stringency can be chosen to favor specific hybridizations (high stringency), which can be used to identify, for example, full-length clones from a library. Less-specific hybridizations (low stringency) can be used to identify related, but not exact (homologous, but not identical), DNA molecules or segments. DNA duplexes are stabilised by: (1) the number of complementary base pairs; (2) the type of base pairs; (3) salt concentration (ionic strength) of the reaction mixture; (4) the temperature of the reaction; and (5) the presence of certain organic solvents, such as formamide, which decrease DNA duplex stability. In general, the longer the probe, the higher the temperature required for proper annealing. A common approach is to vary the temperature; higher relative temperatures result in more stringent reaction conditions. To hybridize under "stringent conditions" describes hybridization protocols in which polynucleotides at least 60% homologous to each other remain hybridized. Generally, stringent conditions are selected to be about 5° C. lower than the thermal melting point (Tm) for the specific sequence at a defined ionic strength and pH. The Tm is the temperature (under defined ionic strength, pH, and polynucleotide concentration) at which 50% of the probes complementary to the given sequence hybridize to the given sequence at equilibrium. Since the given sequences are generally present at excess, at Tm, 50% of the probes are occupied at equilibrium.

"Stringent hybridization conditions" are conditions that enable a probe, amplification primer, or oligonucleotide to hybridize only to its specific sequence—such as a specific target polynucleotide sequence. Stringent conditions are sequence-dependent and will differ. Stringent conditions typically comprise: (1) low ionic strength and high temperature washes, for example 15 mM sodium chloride, 1.5 mM sodium citrate, 0.1% sodium dodecyl sulfate, at 50° C.; (2) a denaturing agent during hybridization, for example, 50% (v/v) formamide, 0.1% bovine serum albumin, 0.1% Ficoll, 0.1% polyvinylpyrrolidone, 50 mM sodium phosphate buffer (750 mM sodium chloride, 75 mM sodium citrate; pH 6.5), at 42° C.; or (3) 50% formamide. Washes typically also comprise 5×SSC (0.75 M NaCl, 75 mM sodium citrate), 50 mM sodium phosphate (pH 6.8), 0.1% sodium pyrophosphate, 5×Denhardt's solution, sonicated salmon sperm DNA (50 μg/mL), 0.1% SDS, and 10% dextran sulfate at 42° C., with a wash at 42° C. in 0.2×SSC (sodium chloride/sodium citrate) and 50% formamide at 55° C., followed by a high-stringency wash consisting of 0.1×SSC containing EDTA at 55° C.

Suitably, the conditions are such that sequences at least about 65%, 70%, 75%, 85%, 90%, 95%, 98%, or 99% homologous to each other typically remain hybridized to each other. "Moderately stringent conditions" use washing solutions and hybridization conditions that are less stringent, such that a polynucleotide will hybridize to the entire, fragments, derivatives, or analogs of the polynucleotide. One example comprises hybridization in 6×SSC, 5×Denhardt's solution, 0.5% SDS and 100 μg/mL denatured salmon sperm DNA at 55° C., followed by one or more washes in 1×SSC, 0.1% SDS at 37° C. The temperature, ionic strength, etc., can be adjusted to accommodate experimental factors such as probe length. Other moderate stringency conditions have been described (see Ausubel et al., Current Protocols in Molecular Biology, Volumes 1-3, John Wiley & Sons, Inc., Hoboken, N.J. (1993); Kriegler, Gene Transfer and Expression: A Laboratory Manual, Stockton Press, New York, N.Y. (1990); Perbal, A Practical Guide to Molecular Cloning, 2nd edition, John Wiley & Sons, New York, N.Y. (1988)).

"Low stringent conditions" use washing solutions and hybridization conditions that are less stringent than those for moderate stringency, such that a polynucleotide will hybridize to the entire, fragments, derivatives, or analogs of the polynucleotide. A non-limiting example of low stringency hybridization conditions includes hybridization in 35% formamide, 5×SSC, 50 mM Tris HCl (pH 7.5), 5 mM EDTA, 0.02% PVP, 0.02% Ficoll, 0.2% BSA, 100 μg/mL denatured salmon sperm DNA, 10% (wt/vol) dextran sulfate at 40° C., followed by one or more washes in 2×SSC, 25 mM Tris HCl (pH 7.4), 5 mM EDTA, and 0.1% SDS at 50° C. Other conditions of low stringency, such as those for cross-species hybridizations, are well-described (see Ausubel et al., 1993; Kriegler, 1990).

The term "plant" refers to any plant at any stage of its life cycle or development, and its progenies. In one embodiment, the plant is a tobacco plant, which refers to a plant belonging to the genus *Nicotiana*. The term includes reference to whole plants, plant organs, plant tissues, plant propagules, plant seeds, plant cells and progeny of same. Plant cells include, without limitation, cells from seeds, suspension cultures, embryos, meristematic regions, callus tissue, leaves, roots, shoots, gametophytes, sporophytes, pollen, and microspores. Suitable species, cultivars, hybrids and varieties of tobacco plant are described herein. One of skill in the art will understand that a variety of materials obtainable or derivable from plants can be used in accordance with the present disclosure, including seedlings, seeds, plants, parts of plants, plant cells, plant tissues, harvested plant material or cured plant material or a combination of two or more thereof. In certain embodiments, the plant material is derived from sterile hybrids-such as sterile tobacco hybrids. The sterile hybrids can be in the form of sterile hybrid crops in (farmer) fields-such as sterile hybrid tobacco crops in (farmer) fields. In certain embodiments, the plant material is not derived from an inbred line-such as an inbred line of a plant crop. Accordingly, the present disclosure may not be used for classifying hybrid seeds. Therefore, the screening of fertile restorer versus sterile versions of inbred lines is not required. "Polynucleotide", "polynucleotide sequence" or "polynucleotide fragment" are used interchangeably herein and refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide. A polynucleotide can be, without limitation, a genomic DNA, complementary DNA (cDNA), mRNA, or antisense RNA or a fragment(s) thereof. Moreover, a polynucleotide can be single-stranded or double-stranded, a mixture of single-stranded and double-stranded regions, a hybrid molecule comprising DNA and RNA, or a hybrid molecule with a mixture of single-stranded and double-stranded regions or a fragment(s) thereof. In addition, the polynucleotide can be composed of triple-stranded regions comprising DNA, RNA, or both or a fragment(s) thereof. A polynucleotide can contain one or more modified bases, such as phosphothioates, and can be a peptide polynucleotide (PNA). Generally, polynucleotides can be assembled from isolated or cloned fragments of cDNA, genomic DNA, oligonucleotides, or individual nucleotides, or a combination of the foregoing. Although the polynucleotides described herein are shown as DNA sequences, the polynucleotides include their corresponding RNA sequences, and their complementary (for example, completely complementary) DNA or RNA sequences, including the reverse complements thereof. Exemplary polynucleotides are set forth in the accompanying sequence listing.

"Target polynucleotide sequence" refers to the polynucleotide sequence to be amplified and/or detected, which in the context of the present disclosure can be a polynucleotide sequence-such as an intergenic spacer associated with sterility (for example, a chloroplastic or mitochondrial intergenic spacer associated with sterility). A target polynucleotide sequence refers to the polynucleotide sequence to be amplified and any complementary second strand. The target polynucleotide sequence may be single-stranded or double-stranded, such that one or both strands can bind to an amplification primer. The amplification primers described herein are designed to anneal to a region of an intergenic spacer associated with sterility (for example, a chloroplastic intergenic spacer associated with sterility).

The term "tobacco" is used in a collective sense to refer to tobacco crops (for example, a plurality of tobacco plants grown in the field and not hydroponically grown tobacco), tobacco plants and parts thereof, including but not limited to, roots, stems, leaves, flowers, and seeds prepared and/or obtained, as described herein. It is understood that "tobacco" refers to *Nicotiana tabacum* plants and products thereof.

The term "tobacco products" refers to consumer tobacco products, including but not limited to, smoking materials (for example, cigarettes, cigars, and pipe tobacco), snuff, chewing tobacco, gum, and lozenges, as well as components, materials and ingredients for manufacture of consumer tobacco products. Suitably, these tobacco products are manufactured from tobacco leaves and stems harvested from tobacco and cut, dried, cured, and/or fermented according to conventional techniques in tobacco preparation.

"Variant" with respect to a polynucleotide means: (i) a portion or fragment of a polynucleotide; (ii) the complement of a polynucleotide or portion thereof; (iii) a polynucleotide that is substantially identical to a polynucleotide of interest or the complement thereof; or (iv) a polynucleotide that hybridizes under stringent conditions to the polynucleotide of interest, complement thereof, or a polynucleotide substantially identical thereto. Variants of the polynucleotides described herein are contemplated.

Unless otherwise defined herein, scientific and technical terms used in connection with the present disclosure shall have the meanings that are commonly understood by those of ordinary skill in the art. For example, any nomenclatures used in connection with, and techniques of, molecular biology, microbiology, plant biology, genetics, polynucleotide chemistry and hybridisation are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

Male Sterility

Several sources for introducing male sterility in to plants are available and have been produced, for example, by the transfer of a plant genome into the cytoplasm of an alien species of the same genus via backcrosses. Cytoplasmic male sterility (CMS) is one favoured mechanism for plant variety protection and for hybrid production. In certain plants—such as tobacco-fertility restoration systems are not needed because the production of interest is the leaves rather than the seeds as in other crops.

CMS is a maternally inherited trait that suppresses production of functional pollen grains. It has been known for over 100 years and has been reported in over 150 plant species. The CMS phenotype is caused by incompatibility of nuclear and cytoplasmic genomes and represents a valuable tool in the production of hybrid seeds.

Source of *Nicotiana* cytoplasms for CMS include cytoplasm from *Nicotiana suaveolens, Nicotiana glauca, Nicotiana bigelovii, Nicotiana plumbaginifolia, Nicotiana megalosiphon* and

*Nicotiana undulata*. The CMS cytoplasms can alter growth rate or cured leaf chemistry but they do not necessarily impact yield or leaf quality.

CMS can be introduced into plants in various ways. For example, if the breeding or the selection is finished and fixed converted lines are available, then one option is to backcross these lines with the sterile version of the same line. After the first generation of backcross (BC1), the converted trait/gene will be heterozygous for all seeds. A second backcross (BC2) of the line with the male sterile progeny of the first generation will produce ½ of a sterile elite line with the desired converted trait in case of 1 gene, ¼ in case of 2 genes and so on. The BC2 lines can be maintained by adding pollen from the fertile converted elite parent each time. The timing of these 2 generations (or 3 to produce enough seeds) is typically 1 to 1.5 years. There is no need to use molecular markers or marker assisted selection in that case.

On the other hand, if the conversion of the elite line is on-going, it is possible to cross the BC1 or BC2 plants of the marker assisted selection project with the CMS elite variety. This allows developing in parallel the sterile and the fertile version of the same variety and because the sterile counterpart is always maintained by backcrossing with the fertile converted line, it will be nearer and nearer genetically as compared to the converted line as the generations advance. The CMS and the converted elite line may be ready almost at the same time in this scenario. A 6 month delay for the availability of the CMS converted line can be expected.

Certain geographical regions tend to have their own preferred genetic source of CMS. For example, in Burley tobacco geographical areas, the CMS standard tends to be a *Nicotiana suaveolens* source of CMS. In flue-cured geographical areas, it tends to be a *Nicotiana glauca* source of CMS. In oriental geographical areas, it tends to be fertile *Nicotiana tabacum* such that a source of sterility is not used.

In accordance with the present disclosure, one or more (suitably, two or more) amplification primers are used to amplify one or more polynucleotide sequences associated with sterility from two or more plant species or varieties-such as *Nicotiana* species. The same polynucleotide sequence(s) associated with sterility are typically amplified from the two or more plant species or varieties. In one embodiment, the one or more polynucleotide sequences associated with sterility from the plant species or varieties are intergenic spacer sequences associated with sterility. In one embodiment, the one or more polynucleotide sequences associated with sterility are one or more polynucleotide sequences associated with CMS. In one embodiment, the one or more polynucleotide sequences associated with sterility are intergenic spacer sequences associated with CMS. Other sequences associated with sterility are described herein. Based on the results of this analysis, it can be readily determined if a batch or lot of plant material is contaminated or adulterated or if a batch or lot of plant material is non-contaminated or non-adulterated.

Polynucleotide Sequences Associated with Sterility

According to the present disclosure, the polynucleotide sequence(s) associated with sterility—such as associated with CMS—for use in the present disclosure will need to be present in various species or varieties of a plant. The size or sequence of the amplified polynucleotide sequence(s) will need to be detectably different in each of the various species or varieties such that the difference in size or sequence can be detected. In other words, the polynucleotide sequence(s) will need to be polymorphic between plant species or varieties. For example, any polynucleotide sequence(s) from the chloroplast or mitochondria that is polymorphic between plant species—such as *Nicotiana tabacum, Nicotiana suaveolens* and *Nicotiana glauca*—can be used. Such polymorphic sequence(s) can be readily identified by, for example, sequencing the organelles of the plant species. In certain embodiments, chloroplastic or mitochondrial intergenic sequences are used as polymorphism is generally greater in the intergenic sequences as compared to genes.

In another embodiment, the polynucleotide sequence(s) associated with sterility is from *Nicotiana suaveolens, Nicotiana glauca, Nicotiana bigelovii, Nicotiana plumbaginifolia, Nicotiana megalosiphon* or *Nicotiana undulata*. In one embodiment, the polynucleotide sequence(s) associated with sterility is an intergenic spacer associated with sterility.

In one embodiment, the intergenic spacer associated with sterility is a chloroplastic or mitochondrial intergenic spacer associated with sterility.

In another embodiment, the intergenic spacer associated with sterility is a chloroplastic intergenic spacer associated from *Nicotiana suaveolens, Nicotiana glauca, Nicotiana bigelovii, Nicotiana plumbaginifolia, Nicotiana megalosiphon* or *Nicotiana undulata*.

In another embodiment, the intergenic spacer associated with sterility is a mitochondrial intergenic spacer associated from *Nicotiana suaveolens, Nicotiana glauca, Nicotiana bigelovii, Nicotiana plumbaginifolia, Nicotiana megalosiphon* or *Nicotiana undulata*. In another embodiment, the chloroplastic intergenic spacer associated with sterility is the trnH-psbA intergenic spacer sequence (GenBank accession number FJ493313.1). This chloroplastic intergenic spacer is associated with CMS. The trnH-psbA chloroplastic intergenic spacer from *Nicotiana tabacum* is set forth in SEQ ID NO: 1. An example of the amplified portion of the trnH-psbA chloroplastic intergenic spacer from *Nicotiana tabacum* is set forth in SEQ ID NO: 2. Exemplary forward and reverse amplification primer sequences are set forth in SEQ ID Nos: 3 and 4, respectively. It will be readily understood by the skilled person that the amplified portion of the trnH-psbA chloroplastic intergenic spacer shown in SEQ ID NO: 2 is an example only and that variations in the sequence of the amplified portion can be tolerated. The important consideration is that the fragment that is chosen to be amplified can have a different size or sequence in other plant species. In the context of the amplified portion shown in SEQ ID NO: 2 for the trnH-psbA chloroplastic intergenic spacer, the amplified portion from *Nicotiana tabacum* is expected at about 483 bp. The amplified portion of the trnH-psbA chloroplastic intergenic spacer from *Nicotiana suaveolens* is expected at about 477 bp. The amplified portion of the trnH-psbA chloroplastic intergenic spacer from *Nicotiana glauca* is expected at about 467 bp. Thus, the size of the amplified portion from each species is different which allows the size or the sequence of the amplified fragment to be used as a marker to identify from which plant species the chloroplastic intergenic spacer is derived.

In another embodiment, the chloroplastic intergenic spacer associated with sterility is the trnL-trnF chloroplastic intergenic spacer. This chloroplastic intergenic spacer is associated with CMS. The trnL-trnF chloroplastic intergenic spacer from *Nicotiana tabacum* is set forth in SEQ ID NO: 5. The corresponding sequence from *Nicotiana glauca* is disclosed in Genbank Accession number AJ577414. The corresponding sequence from *Nicotiana suaveolens* is disclosed in Genbank Accession number AJ577410. An example of the amplified portion of the trnL-trnF chloroplastic intergenic spacer from *Nicotiana tabacum* is set forth in SEQ ID NO: 6. Exemplary forward and reverse amplification primer sequences are set forth in SEQ ID Nos: 7 and 8, respectively. For the same reasons as noted above, the sequence of the amplified portion and the sequence of the amplification primers is only exemplary. The amplified portion of the trnL-trnF chloroplastic intergenic spacer from *Nicotiana tabacum* is expected at about 483 bp. The amplified portion of the trnL-trnF chloroplastic intergenic spacer from *Nicotiana suaveolens* is expected at about 477 bp. The amplified portion of the trnH-psbA chloroplastic intergenic spacer from *Nicotiana glauca* is expected at about 467 bp.

In another embodiment, the chloroplastic intergenic spacer associated with sterility is the atpH-atpI chloroplastic intergenic spacer (nucleotides 14192-15350 of *Nicotiana tabacum* cultivar TN90 plastid—GenBank accession number: KU199713.1). This chloroplastic intergenic spacer is associated with CMS.

In another embodiment, the chloroplastic intergenic spacer associated with sterility is the ndhC-trnV chloroplastic intergenic spacer (nucleotides 52761-53848 of *Nicotiana tabacum* cultivar TN90 plastid—GenBank accession number: KU199713.1). This chloroplastic intergenic spacer is associated with CMS.

In another embodiment, the chloroplastic intergenic spacer associated with sterility is the petA-psbJ chloroplastic intergenic spacer (nucleotides 65390-66456 of *Nicotiana tabacum* cultivar TN90 plastid—GenBank accession number: KU199713.1). This chloroplastic intergenic spacer is associated with CMS.

In another embodiment, the chloroplastic intergenic spacer associated with sterility is the petN-psbM chloroplastic intergenic spacer (nucleotides 29720-30853 of *Nicotiana tabacum* cultivar TN90 plastid—GenBank accession number: KU199713.1). This chloroplastic intergenic spacer is associated with CMS.

In another embodiment, the chloroplastic intergenic spacer associated with sterility is the psbE-petL chloroplastic intergenic spacer (nucleotides 67222-68386 of *Nicotiana tabacum* cultivar TN90 plastid—GenBank accession number: KU199713.1). This chloroplastic intergenic spacer is associated with CMS.

In another embodiment, the chloroplastic intergenic spacer associated with sterility is the psbM-trnD chloroplastic intergenic spacer (nucleotides 30957-32028 of *Nicotiana*

*tabacum* cultivar TN90 plastid—GenBank accession number: KU199713.1). This chloroplastic intergenic spacer is associated with CMS.

In another embodiment, the chloroplastic intergenic spacer associated with sterility is the rbc1-accD chloroplastic intergenic spacer (nucleotides 59121-59886 of *Nicotiana tabacum* cultivar TN90 plastid—GenBank accession number: KU199713.1). This chloroplastic intergenic spacer is associated with CMS.

In another embodiment, the chloroplastic intergenic spacer associated with sterility is the rpoD-trnC chloroplastic intergenic spacer (nucleotides 27604-28889 of *Nicotiana tabacum* cultivar TN90 plastid—GenBank accession number: KU199713.1). This chloroplastic intergenic spacer is associated with CMS.

In another embodiment, the chloroplastic intergenic spacer associated with sterility is the rps16-trnQ chloroplastic intergenic spacer (nucleotides 6302-7508 of *Nicotiana tabacum* cultivar TN90 plastid—GenBank accession number: KU199713.1). This chloroplastic intergenic spacer is associated with CMS.

In another embodiment, the chloroplastic intergenic spacer associated with sterility is the trnS-trnG chloroplastic intergenic spacer (nucleotides 8811-9591 of *Nicotiana tabacum* cultivar TN90 plastid—GenBank accession number: KU199713.1). This chloroplastic intergenic spacer is associated with CMS.

In another embodiment, the chloroplastic intergenic spacer associated with sterility is the trn T-psbD chloroplastic intergenic spacer (nucleotides 33345-34563 of *Nicotiana tabacum* cultivar TN90 plastid—GenBank accession number: KU199713.1). This chloroplastic intergenic spacer is associated with CMS.

In another embodiment, the chloroplastic intergenic spacer associated with sterility is the trnW-psaJ chloroplastic intergenic spacer (nucleotides 68981-69658 of *Nicotiana tabacum* cultivar TN90 plastid—GenBank accession number: KU199713.1). This chloroplastic intergenic spacer is associated with CMS.

In another embodiment, the chloroplastic intergenic spacer associated with sterility is the ycf1 chloroplastic intergenic spacer (nucleotides 125979-131687 of *Nicotiana tabacum* cultivar TN90 plastid—GenBank accession number: KU199713.1). This chloroplastic intergenic spacer is associated with CMS.

In certain embodiments, the chloroplastic intergenic spacer associated with sterility is not the TrnH-TrnK chloroplastic intergenic spacer (nucleotides 168-1900 of *Nicotiana tabacum* cultivar TN90 plastid—GenBank accession number: KU199713.1).

Amplification

In accordance with the present disclosure, a sample of polynucleotide from a batch or lot of plant material is provided for analysis. The plant material can be, for example, seedlings, seeds, plants, parts of plants, harvested plant material or cured plant material or a combination of two or more thereof. Suitably, the plant material is sterile hybrid plant material. More suitably, the plant material is sterile hybrid tobacco material.

The sample of polynucleotide is contacted with one or more amplification primers that are capable of amplifying the target polynucleotide sequence(s) associated with sterility. An in vitro polynucleotide amplification reaction is then carried out on the sample to generate an amplification product.

Amplification methods for use in the present disclosure are well known in the art and include, for example, replicase-mediated amplification, polymerase chain reaction (PCR), ligase chain reaction (LCR), strand-displacement amplification (SDA), thermophilic strand displacement amplification (tSDA), self-sustained sequence replication (3SR), transcription-mediated or transcription-associated amplification (TMA), polynucleotide sequence-based amplification (NASBA), ligase chain reaction (LCR) and rolling circle amplification (RCA). Such amplification methods are well-known in the art and are readily used in accordance with the present disclosure. The amplification technique can be isothermal and conducted at a constant temperature, or thermal which requires cycling between high and low temperatures. In certain embodiments, the use of PCR is preferred.

For in vitro polynucleotide amplification reactions to be carried out, the use of one or more, suitably, two or more amplification primers is required. The design of amplification primers can be optimised for each method of amplification. As no special sequences or structures are required to drive the amplification reaction, amplification primers for a PCR may consist only of template binding sequences. However, other amplification reactions may require more specialised nucleotide sequences, in addition to the target binding sequence, in order for the reaction to proceed. For example, an amplification primer for use in a SDA assay further comprises a restriction endonuclease recognition site 5' to the target binding sequence. The amplification primer may also comprise a 3'-OH group, which is extendable by DNA polymerase when the template-binding sequence of the amplification primer is annealed to the target polynucleotide sequence. Amplification primers for 3SR and NASBA, in contrast, comprise an RNA polymerase promoter near the 5' end. The promoter is appended to the target binding sequence and serves to drive the amplification reaction by directing transcription of multiple RNA copies of the template. Such sequences in addition to the target binding sequence that are necessary for a particular amplification reaction are well known in the art.

In designing amplification primers for use the present disclosure, general concerns known in the art will be taken into account. For example, when a target polynucleotide sequence comprising a large number of GC and AT repeats is used for designing a primer, care should be taken to minimize potential dimer interactions to avoid self-hybridization of primers. Primers that can form four or more consecutive bonds with itself, or eight or more inter-strand bonds with other primers should be generally avoided. Primers that can form 3' dimers should especially be avoided, because hybridizing at the 3' ends of the primer, even transiently, will lead to extension of the primer due to polymerase action and ruining of the primer. Certain computer software programs can be used in designing of the primers to avoid the problems. Primer combinations are also screened for optimal conditions.

As is known in the art, annealing or hybridisation of complementary and partially complementary polynucleotide sequences may also be obtained by adjustment of the reaction conditions to increase or decrease stringency (e.g., adjustment of temperature or salt content of the buffer).

Polynucleotide amplification primers comprising about 10 or more contiguous polynucleotides that are complementary to the target polynucleotide sequence to be amplified are described. The primers may comprise or consist of about 15, 20, 25, 30, 40, 45 or 50 more contiguous polynucleotides that hybridise (for example, specifically hybridise) to the target polynucleotide sequence(s) described herein. In some embodiments, the primers may comprise or consist of about 10 to 50 contiguous nucleotides, about 10 to 40 contiguous nucleotides, about 10 to 30 contiguous nucleotides or about 15 to 30 contiguous nucleotides. The amplification primer(s) can be designed and used to amplify or detect a part or all of the target polynucleotide sequence. By way of specific example, two amplification primers may be used in a PCR protocol to amplify a target polynucleotide sequence. The PCR may also be performed using one primer that is derived from a polynucleotide sequence and a second primer that hybridises to the sequence upstream or downstream of the polynucleotide sequence-such as a promoter sequence, the 3' end of the mRNA precursor or a sequence derived from a vector. Thus, in some embodiments, a pair of amplification primers is used, each of which anneals to one of the two strands of a double stranded target polynucleotide sequence. In this case, amplification is exponential because both the sense and antisense strands serve as templates for the opposite primer in subsequent rounds of amplification. When a single amplification primer is used, amplification is linear because only one strand serves as a template for primer extension.

The amplification primers described herein can be 100% complementary to their target polynucleotide sequence. However, based on the primer design conditions described above, primers and probes can bind to target polynucleotide sequences even though they are less than 100% complementary with those regions. The requisite degree of complementarity depends on a variety of factors including the stringency of the binding conditions. Depending upon the stringency conditions employed, the amplification primers may be modified to include different bases in their sequence and still be sufficiently complementary to bind to the target region. Sufficiently complementary, as used herein includes complementarity of 70% or more. In preferred embodiments, the complementarity of the amplification primers to their target polynucleotide sequence is at least 80% over the length of the binding portion of the amplification primers. More preferably, the complementarity of the amplification primers to their target polynucleotide sequences is 90% or more.

Suitably, the amplification primers according to the present disclosure are designed to specifically amplify a polynucleotide sequence associated with sterility, as described herein. Suitably, the amplification primers are designed such that they have at least 90%, 95% or 100% complementarity to the polynucleotide sequence associated with sterility.

In designing the amplification primers for use in the present disclosure it is important to design them such that the target polynucleotide sequence associated with sterility can be amplified from more than one different plant species or variety. Thus, the sequence of the amplification primer(s) will be at least 90%, 95% or 100% complementarity to the polynucleotide sequence associated with sterility from the more than one different plant species or varieties. In designing the amplification primers for use in the present disclosure it is also important to design them such that the sequence that is amplified will have a different size or sequence when it is amplified from each different plant species or variety. Thus, in one embodiment, the amplification primers are configured to amplify polymorphic sequences within the *Nicotiana* genus. Accordingly, size or sequence of the amplification product can then be used as a marker to decipher from which plant species or variety the amplification product is derived. The size of the amplification product is typically designed to be 500 base pairs or less, suitably, 400 base pair pairs or less, suitably, 300 base pairs or less, or suitably, 200 base pairs or less.

The use of chloroplastic or mitochondrial intergenic spacers according to one embodiment of the present disclosure can be advantageous because the chloroplastic or mitochondrial genome in higher plants is highly conserved, which has had some practical implications for genetic research. Therefore universal PCR primer pairs can be designed on the basis of conserved coding sequences of chloroplast or mitochondrial DNA to amplify the DNA located from different plant species.

Suitably, a restriction enzyme digestion step is not required for differentiating the amplification product(s). This can make the method faster and simpler.

The amplification products generated can be detected by any method known in the art. Amplification products can be detected by hybridization to a labeled probe using conventional techniques, for example, one that hybridizes to amplified polynucleotides at a sequence that lies between the amplification primers. Desirably, amplification products are detected by their size or by their sequence, as discussed more fully below.

Suitably, the amplification product is analysed directly without any of processing of the amplification product before the size and/or sequence of the amplification product is determined. Thus, for example, the amplification product is not digested (for example, with a restriction endonuclease) prior to the size and/or sequence of the amplification product being determined. Advantageously, this makes the method faster and simpler.

Methods for Determining the Sequence of an Amplification Product(s)

The amplified sequence(s) can differ in sequence by at least 1 nucleotide, at least 2 nucleotides, at least 3 nucleotides, at least 4 nucleotides, at least 5 nucleotides, at least 6 nucleotides, at least 7 nucleotides, at last 8 nucleotides, at least 9 nucleotides or at least 10 nucleotides. Suitably, the amplified sequence(s) can differ in sequence by at least 5 nucleotides, at least 6 nucleotides, at least 7 nucleotides, at last 8 nucleotides, at least 9 nucleotides or at least 10 nucleotides. Suitably, the amplified sequence(s) can differ in sequence by at least 10 nucleotides, at least 20 nucleotides, at least 30 nucleotides, at last 40 nucleotides, or at least 50 nucleotides.

Various methods are available in the art for determining the sequence of the amplification product. Various methods are available in the art for determining the presence of one or more polymorphisms in an amplification product, including determining the presence or absence of one or more single nucleotide polymorphisms. Such methods include direct sequencing of the amplification product, amplification product polymorphism assays, polynucleotide hybridisation assays and computer based methods. Commercially available method, kits or services for performing these methods are widely available and are well known to the skilled person.

For direct sequencing methods, the amplification product is sequenced using any suitable method-such as manual sequencing or automated sequencing—wherein the nucleotide sequence of the amplification product is determined. To determine the sequence of the amplification product, the polynucleotide sample is first subjected to a sequencing reaction-such as Sanger dideoxy sequencing. This method relies upon the template-directed incorporation of nucleotides onto an annealed primer by a DNA polymerase from a mixture containing deoxy- and dideoxynucleotides. The incorporation of dideoxynucleotides results in chain termination due to the inability of the enzyme to catalyze further extension of the strand. Separation of reaction products results in a "ladder" of extension products wherein each extension product ends in a particular dideoxynucleotide complementary to the nucleotide opposite it in the template. Extension products may be detected in several ways, including for example, the inclusion of fluorescently-labeled primers, deoxynucleotide triphosphates or dideoxynucleotide triphosphates in the reaction. The sequencing reaction product may then be analyzed by a variety of means, most generally by capillary gel electrophoresis, and/or polyacrylamide gel electrophoresis and the like.

Polymorphism(s) may also be determined using a polynucleotide amplification assay in which oligonucleotide primers are designed to specifically amplify a fragment containing one or more polymorphisms.

Polymorphism(s) may also be detected using fragment length polymorphism assays, in which a unique DNA banding pattern based on cleaving the DNA at a series of positions is generated using an enzyme—such as a restriction endonuclease. DNA fragments from a sample containing one or more polymorphisms will have a different banding pattern than a wild type sequence.

Polymorphism(s) may also be detected by fragment sizing analysis.

Polymorphism(s) may also be detected using a restriction fragment length polymorphism assay (RPLP). The region of interest is first isolated using PCR. The PCR products are then cleaved with restriction enzymes known to give a unique length fragment for a given polymorphism. The restriction-enzyme digested PCR products are separated by agarose gel electrophoresis and visualized by ethidium bromide staining, or other means know in the art, and compared to controls-such as wild-type.

Polymorphism(s) may also be detected using a cleavase fragment length polymorphism assay as described in, for example, U.S. Pat. No. 5,888,750.

Polymorphism(s) may also be detected using a hybridization assay, in which the presence or absence of a polymorphism is determined based on the ability of the DNA from the sample to hybridize to a complementary DNA molecule-such as an oligonucleotide probe. A variety of hybridization assays are available. The hybridized polynucleotides can be detected using one or more labels attached to the sample polynucleotides. The labels may be incorporated by any of a number of means well known to those of skill in the art.

Polymorphism(s) may also be detected using a DNA chip hybridization assay, in which a series of oligonucleotide probes are affixed to a solid support. The oligonucleotide probes are designed to be unique to a given single nucleotide polymorphism. The DNA sample of interest is contacted with the DNA chip and hybridization is detected (see, for example, U.S. Pat. No. 6,045,996). The amplification product can be labeled and incubated with the array, which is then inserted into a scanner, where patterns of hybridisation can be detected and collected. Since the sequence and positions of each probe on the array are known the identity of the target polynucleotide applied to the probe array can be determined.

Polymorphism(s) may be detected using a DNA microchip containing electronically captured probes as described in U.S. Pat. No. 6,068,818.

Polymorphism(s) may also be detected using a bead array for the detection of polymorphisms, as described in WO00/39587.

Methods for Determining the Size of an Amplification Product(s)

The difference in size(s) of the amplified polynucleotide(s) can be at least 1 nucleotide, at least 2 nucleotides, at least 3 nucleotides, at least 4 nucleotides, at least 5 nucleotides, at least 6 nucleotides, at least 7 nucleotides, at last 8 nucleotides, at least 9 nucleotides or at least 10 nucleotides. Suitably, the difference in size(s) of the amplified polynucleotide(s) can be at least 5 nucleotides, at least 6 nucleotides, at least 7 nucleotides, at last 8 nucleotides, at least 9 nucleotides or at least 10 nucleotides. Suitably, the difference in size(s) of the amplified polynucleotide(s) can be at least 10 nucleotides, at least 20 nucleotides, at least 30 nucleotides, at last 40 nucleotides, or at least 50 nucleotides.

The amplified polynucleotide may be analysed based on size using methods that are well known in the art—such as gel electrophoresis, anion-exchange chromatography, size-exclusion chromatography, pulse-field electrophoresis, sieving gel electrophoresis, capillary electrophoresis or Southern analysis.

Gel electrophoresis is a technique which is frequently used to separate polynucleotide molecules based on size. The gel is typically comprised of algal polysaccharide agarose, or for separation of smaller nucleic fragments a polyacrylamide gel may be used. For analysis, the polynucleotide sample is placed into a well formed in the gel, and an electrical field is applied. The negative charge of the polynucleotide will result in migration of the polynucleotide through the gel towards the positive pole. The composition of the gel alters the speed of migration of molecules such that separation is achieved. Variations of gel electrophoresis that are contemplated herein include pulsed-field gel electrophoresis and sieving agarose gel electrophoresis.

Another analytical procedure that may be useful is the analysis of amplified nucleic fragments by Southern Analysis.

In a preferred embodiment, the amplified polynucleotide is analyzed by capillary gel electrophoresis. The physical characteristics of the capillaries are important for resolving the components of interest in a sample and are typically <100 μm internal diameter and 20-100 cm in length, although the capillaries are not necessarily limited to these dimensions. Various polymeric networks may be used including those comprised of cellulosic material, polyethylene oxide, polyethylene glycol, hydroxypropylmethyl cellulose, hydroxyethyl cellulose or methyl cellulose. The polymeric network is normally suspended in a biological buffer. The sample can be introduced into the inlet of a capillary by various techniques-such as electrokinetic injection or hydrodynamic injection.

Classifying a Batch of Plant Material

Based on the results of the analysis that is performed according to the present disclosure, a batch of plant material can be classified as either being contaminated or adulterated or being non-contaminated or non-adulterated. Suitably the plant material is classified as either being contaminated or adulterated or being non-contaminated or non-adulterated with plant material of a different origin. Plant material of a different origin can be plant material that is expected to be fertile, or plant material that lacks the expected source of sterility, or plant material that has a distinguishably different genetic source of sterility.

Typically, the fertility status of the batch or lot of plant material will be known prior to carrying out the method or analysis. Generally, prepared tobacco material—such as seeds or seedlings—are often sold in non-fertile form and the genetic source of this sterility of the prepared tobacco seeds will be known. The tobacco seeds or seedlings may also be sold in fertile form. For example, in Burley tobacco geographical areas, the CMS standard tends to be a *Nicotiana suaveolens* source of CMS. In flue-cured geographical areas, it tends to be a *Nicotiana glauca* source of CMS. In oriental geographical areas, it tends to be fertile *Nicotiana tabacum* such that a source of sterility is not used.

Thus, by way of example, the source of sterility in commercially supplied tobacco seeds may be CMS from *Nicotiana suaveolens* cytoplasm. According to the method of the present disclosure, once the size or sequence of the amplified target polynucleotide sequence(s) of the polynucleotide(s) associated with sterility from the batch of plant material has been determined, it can be compared to the size or sequence of known amplification products from known genetic sources of sterility. Then, according to the results of this step, if the genetic source of sterility corresponds to the expected genetic source of sterility of the batch of plant material then the batch of plant material is considered to be non-contaminated or non-adulterated. If the genetic source of sterility does not correspond to the genetic source of sterility of the batch of plant material then the batch of plant material is considered to be contaminated or adulterated. In the event that the batch of plant material is found to be non-contaminated or non-adulterated then it can be expected that the plant material is free from contamination and that the plant material derived therefrom will be of the expected quality or purity. In the event that the batch of plant material is found to be contaminated or adulterated then it can be expected that the plant material has been contaminated with plant material from other sources and that the plant material derived therefrom will not be of the expected quality or purity. In this case, the plant material may need to be discarded or destroyed as the quality or purity thereof cannot be assured.

By way of further example, a batch of plant material supplied for testing can have a source of sterility of CMS from *Nicotiana suaveolens* cytoplasm. A sample of polynucleotide is extracted from this plant material and a target polynucleotide sequence(s) of a cytoplasmic intergenic spacer associated with CMS is amplified. The size or sequence of the amplification product(s) is determined and based on the size or sequence of the amplification product(s) the genetic source of sterility is identified by comparing the size or sequence of the amplification product with the size or sequence of amplification products from the same cytoplasmic intergenic spacer associated with CMS. Thus, in the context of this example, the size or sequence of the amplification product(s) will be compared with the size or sequence of known amplification products from known genetic sources of CMS sterility that are used in tobacco. If it is determined from the amplification step that the size or sequence of the amplification product(s) corresponds only to the source of CMS sterility from *Nicotiana suaveolens* cytoplasm then it can be determined that the plant material is not contaminated or not adulterated. If it is determined from the amplification step that the size or sequence of the amplification product(s) does not correspond to the source of CMS sterility from *Nicotiana suaveolens* cytoplasm then it can be determined that the plant material is contaminated or adulterated. So, for example, the size or sequence of the amplification product(s) may correspond to the source of CMS sterility from *Nicotiana glauca, Nicotiana bigelovii, Nicotiana plumbaginifolia, Nicotiana megalosiphon* or *Nicotiana undulata* cytoplasm or the size or sequence of the amplification product may correspond to *Nicotiana tabacum* cytoplasm thereby indicating the presence of fertile tobacco material. In this example, the plant material may need to be discarded or destroyed as the quality or purity thereof cannot be assured.

By way of further example, a batch of plant material supplied for testing can have CMS sterility from *Nicotiana glauca* cytoplasm. A sample of polynucleotide is extracted from this plant material and a target polynucleotide sequence(s) of a cytoplasmic intergenic spacer associated with CMS is amplified. The size or sequence of the amplification product(s) is determined and based on the size or sequence of the amplification product(s) the genetic source of sterility is identified by comparing the size or sequence of the amplification product(s) with the size or sequence of amplification products from the same cytoplasmic intergenic spacer associated with CMS. Thus, in the context of this example, the size or sequence of the amplification product(s) will be compared with the size or sequence of known amplification products from known genetic sources of CMS sterility that are used in tobacco. If it is determined from the amplification step that the size or sequence of the amplification product(s) corresponds only to the source of CMS sterility from *Nicotiana glauca* cytoplasm then it can be determined that the plant material is not contaminated or not adulterated. If it is determined from the amplification step that the size or sequence of the amplification product(s) does not correspond to the source of CMS sterility from *Nicotiana glauca* cytoplasm then it can be determined that the plant material is contaminated or adulterated. So, for example, the size or sequence of the amplification product(s) may correspond to the source of CMS sterility from *Nicotiana suaveolens, Nicotiana bigelovii, Nicotiana plumbaginifolia, Nicotiana megalosiphon* or *Nicotiana undulata* cytoplasm or the size or the sequence of the amplification product(s) may correspond to *Nicotiana tabacum* cytoplasm thereby indicating the presence of fertile tobacco material. In this example, the plant material may need to be discarded or destroyed as the quality or purity thereof cannot be assured.

By way of further example, a batch of plant material supplied for testing can be fertile *Nicotiana tabacum*. A sample of polynucleotide is extracted from this plant material and a target polynucleotide sequence(s) of a cytoplasmic intergenic spacer associated with CMS is amplified. The size or sequence of the amplification product(s) is determined and based on the size or sequence of the amplification product(s) the genetic source of sterility is identified by comparing the size or sequence of the amplification product(s) with the size or sequence of amplification products from the same cytoplasmic intergenic spacer associated with CMS. In this example, it will be expected that no amplification products will be obtained in non-contaminated or non-adulterated plant material as the plant material does not have a genetic source of CMS. If it is determined from the amplification step that no amplification product is present then it can be determined that the plant material is not contaminated or not adulterated. If it is determined from the amplification step that an amplification product(s) is obtained from a source of CMS sterility then it can be determined that the plant material is contaminated or adulterated. In this example, the plant material may need to be discarded or destroyed as the quality or purity thereof cannot be assured.

A method for classifying a batch of plant material plant material as either being contaminated or non-contaminated comprising the use of one or more amplification primers specific for a polynucleotide sequence associated with sterility is also disclosed.

The use of two or more amplification primers specific for a polynucleotide sequence associated with sterility for classifying a batch of plant material as either being contaminated or non-contaminated is also disclosed.

Multiple amplification products may be obtained which is indicative that multiple different genetic sources of sterility are present in the sample. Typically, this will be indicative of contamination or adulteration.

Determining Conformity

Based on the results of the analysis that is performed according to the present disclosure, the conformity of a batch or lot of plant material can be determined. In determining the conformity of a batch or lot of plant material it may determined if the batch or lot of plant material conforms to a standard. For example, certain geographical regions have a standardised genetic source of CMS. For example, in Burley tobacco geographical areas, the CMS standard tends to be a *Nicotiana suaveolens* source of CMS. In flue-cured geographical areas, the CMS standard tends to be a *Nicotiana glauca* source of CMS. In oriental geographical areas, the CMS standard tends to be fertile *Nicotiana tabacum* such that a source of sterility is not used. Thus, in a further aspect, there is provided a method for checking the conformity of a batch of plant material comprising: (i) providing a sample of polynucleotide from the batch of plant material; (ii) contacting the sample of polynucleotide with amplification primers to amplify a target polynucleotide sequence(s) associated with sterility; (iii) performing an in vitro polynucleotide amplification reaction on the sample to generate an amplification product(s); (iv) determining the size or sequence of the amplification product(s); and (v) based on the size or sequence of the amplification product determined in step (iv) comparing the size or sequence of the amplification product(s) with the size or sequence of known amplification products from known genetic sources of sterility; wherein if the genetic source of sterility determined in step (v) corresponds to the expected genetic source of sterility of the batch of plant material then said batch of plant material is considered to be conforming; or wherein if the genetic source of sterility determined in step (v) does not correspond to the expected genetic source of sterility of the batch of plant material then said batch of plant material is considered to be non-conforming.

According to this method, once the size or sequence of the amplified target polynucleotide sequence(s) associated with sterility from the batch of plant material has been determined, it can be compared to the size or sequence of known amplification products from known genetic sources of sterility. Then, according to the results of this step, if the genetic source of sterility corresponds to the expected genetic source of sterility of the batch of plant material then the batch of plant material is considered to be conforming (for example, not adulterated). If the genetic source of sterility does not correspond to the expected genetic source of sterility of the batch of plant material then the batch of plant material is considered to be non-conforming (for example, adulterated). In the event that the batch of plant material is found to be conforming then it can be expected that the plant material is free from contamination or adulteration and that the plant material derived therefrom will be of the expected quality or purity. In the event that the batch of plant material is found to be non-conforming or adulterated then it can be expected that the plant material has been contaminated with plant material from other sources and that the plant material derived therefrom will not be of the expected quality or purity. In this case, the plant material may need to be discarded or destroyed as the quality or purity thereof cannot be assured.

By way of example, a batch of plant material supplied for testing can have an expected genetic source of CMS from *Nicotiana suaveolens* cytoplasm. A sample of polynucleotide is extracted from this plant material and a target polynucleotide sequence(s) of a cytoplasmic intergenic spacer associated with CMS is amplified. The size or sequence of the amplification product(s) is determined and based on the size or sequence of the amplification product the genetic source of sterility is identified by comparing the size or sequence of the amplification product(s) with the size or sequence of amplification products from the same cytoplasmic intergenic spacer associated with CMS. Thus, in the context of this example, the size or sequence of the amplification product(s) will be compared with the size or sequence of known amplification products from known genetic sources of CMS sterility that are used in tobacco. If it is determined from the amplification step that the size or sequence of the amplification product(s) corresponds only to the source of CMS sterility from *Nicotiana suaveolens* cytoplasm then it can be determined that the plant material is conforming or not adulterated. If it is determined from the amplification step that the size or sequence of the amplification product(s) does not correspond to the source of CMS sterility from *Nicotiana suaveolens* cytoplasm then it can be determined that the plant material is non-conforming or adulterated. So, for example, the size or sequence of the amplification product(s) may correspond to the source of CMS sterility from *Nicotiana glauca, Nicotiana bigelovii, Nicotiana plumbaginifolia, Nicotiana megalosiphon* or *Nicotiana undulata* cytoplasm or the size or sequence of the amplification product(s) may correspond to *Nicotiana tabacum* cytoplasm thereby indicating the presence of fertile tobacco material. In this example, the plant material may need to be discarded or destroyed as the quality or purity thereof cannot be assured.

By way of further example, a batch of plant material supplied for testing can have an expected genetic source of CMS from *Nicotiana glauca* cytoplasm. A sample of polynucleotide is extracted from this plant material and a target polynucleotide sequence(s) of a cytoplasmic intergenic spacer associated with CMS is amplified. The size or sequence of the amplification product(s) is determined and based on the size or sequence of the amplification product(s) the genetic source of sterility is identified by comparing the size or sequence of the amplification product(s) with the size or sequence of amplification products from the same cytoplasmic intergenic spacer associated with CMS. Thus, in the context of this example, the size or sequence of the amplification product(s) will be compared with the size or sequence of known amplification products from known genetic sources of CMS sterility that are used in tobacco. If it is determined from the amplification step that the size or sequence of the amplification product(s) corresponds only to the source of CMS sterility from *Nicotiana glauca* cytoplasm then it can be determined that the plant material is conforming or not adulterated. If it is determined from the amplification step that the size or sequence of the amplification product(s) does not correspond to the source of CMS sterility from *Nicotiana glauca* cytoplasm then it can be determined that the plant material is non-conforming or adulterated. So, for example, the size or sequence of the amplification product may correspond to the source of CMS sterility from *Nicotiana suaveolens, Nicotiana bigelovii, Nicotiana plumbaginifolia, Nicotiana megalosiphon* or *Nicotiana undulata* cytoplasm or the size or the sequence of the amplification product may correspond to *Nicotiana tabacum* cytoplasm thereby indicating the presence of fertile tobacco material. In this example, the plant material may need to be discarded or destroyed as the quality or purity thereof cannot be assured.

By way of further example, a batch of plant material supplied for testing can be fertile *Nicotiana tabacum*. A sample of polynucleotide is extracted from this plant material and a target polynucleotide sequence(s) of a cytoplasmic intergenic spacer associated with CMS is amplified. The size or sequence of the amplification product(s) is determined and based on the size or sequence of the amplification product(s) the genetic source of sterility is identified by comparing the size or sequence of the amplification product with the size or sequence of amplification products from the same cytoplasmic intergenic spacer associated with CMS. In this example, it will be expected that no amplification products will be obtained in conforming plant material as the plant material does not have a genetic source of CMS. If it is determined from the amplification step that no amplification product is present then it can be determined that the plant material is conforming. If it is determined from the amplification step that an amplification product(s) is obtained from a source of CMS sterility then it can be determined that the plant material is non-conforming. In this example, the plant material may need to be discarded or destroyed as the quality or purity thereof cannot be assured. Multiple amplification products may be obtained which is indicative that multiple different genetic sources of sterility are present in the sample. Typically, this will be indicative of contamination or adulteration.

A method for checking the conformity of a batch of plant material comprising the use of one or more amplification primers specific for a polynucleotide sequence associated with sterility is also disclosed.

The use of two or more amplification primers specific for a polynucleotide sequence associated with sterility for checking the conformity of a batch of plant material is also disclosed.

Plants

Plants and plant material derived therefrom suitable for use in the present disclosure include monocotyledonous and dicotyledonous plants. Suitable species may include members of the genera *Nicotiana*, including *N. rustica* and *N. tabacum* (for example, LA B21, LN KY171, TI 1406, Basma, *Galpao*, Perique, Beinhart 1000-1, and Petico). Other species include *N. acaulis, N. acuminata, N. africana, N. alata, N. ameghinoi, N. amplexicaulis, N. arentsii, N. attenuata, N. azambujae, N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora, N. maritima, N. megalosiphon, N. miersii, N. noctiflora, N. nudicaulis, N. obtusifolia, N. occidentalis, N. occidentalis* subsp. *hesperis, N. otophora, N. paniculata, N. pauciflora, N. petunioides, N. plumbaginifolia, N. quadrivalvis, N. raimondii, N. repanda, N. rosulata, N. rosulata* subsp. *ingulba, N. rotundifolia, N. setchellii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica, N. undulata, N. velutina, N. wigandioides*, and N. x sanderae. In one embodiment, the use of varieties of *N. tabacum* is contemplated.

*Nicotiana tabacum* varieties include Burley type, dark type, flue-cured type, and Oriental type tobaccos. Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF911, DT 538 LC Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KY14×L8 LC, Little Crittenden, McNair 373, McNair 944, msKY 14×L8, Narrow Leaf Madole, Narrow Leaf Madole LC, NBH 98, N-126, N-777LC, N-7371LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, VA359, AA 37-1, B13P, Xanthi (Mitchell-Mor), Bel-W3, 79-615, Samsun Holmes NN, KTRDC number 2 Hybrid 49, Burley 21, KY8959, KY9, MD 609, PG01, PG04, PO1, PO2, PO3, RG11, RG 8, VA509, AS44, Banket A1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpão Comum, HB04P, Hicks Broadleaf, Kabakulak Elassona, Kutsage E1, LA BU 21, NC 2326, NC 297, PVH 2110, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, Basma xanthi, GR149, GR153, Petit Havana. Low converter subvarieties of the above, even if not specifically identified herein, are also contemplated.

The use of tobacco cultivars and elite tobacco cultivars is also contemplated herein.

Consumable Products

The plant material that is tested as described herein, particularly the leaf lamina and midrib of such plants, can be incorporated into or used in making various consumable products, including but not limited to, aerosol forming materials, aerosol forming devices, smoking articles, smokable articles, smokeless products, medicinal or cosmetic products, intravenous preparations, tablets, powders, and tobacco products. Examples of aerosol forming materials include tobacco compositions, tobaccos, tobacco extract, cut tobacco, cut filler, cured tobacco, expanded tobacco, homogenized tobacco, reconstituted tobacco, and pipe tobaccos. Smoking articles and smokable articles are types of aerosol forming devices. Examples of smoking articles or smokable articles include cigarettes, cigarillos, and cigars. Examples of smokeless products comprise chewing tobaccos, and snuffs. In certain aerosol forming devices, rather than combustion, a tobacco composition or another aerosol forming material is heated by one or more electrical heating elements to produce an aerosol. In another type of heated aerosol forming device, an aerosol is produced by the transfer of heat from a combustible fuel element or heat source to a physically separate aerosol forming material, which may be located within, around or downstream of the heat source. Smokeless tobacco products and various tobacco-containing aerosol forming materials may contain tobacco in any form, including as dried particles, shreds, granules, powders, or a slurry, deposited on, mixed in, surrounded by, or otherwise combined with other ingredients in any format, such as flakes, films, tabs, foams, or beads. As used herein, the term 'smoke' is used to describe a type of aerosol that is produced by smoking articles, such as cigarettes, or by combusting an aerosol forming material.

The plant material that is tested can be cured plant material. Processes of curing green tobacco leaves are known by those having skills in the art and include without limitation air-curing, fire-curing, flue-curing and sun-curing as described herein.

The invention is further described in the Examples below, which are provided to describe the invention in further detail. These examples, which set forth a preferred mode presently contemplated for carrying out the invention, are intended to illustrate and not to limit the invention.

EXAMPLES

Example 1: Method for Amplifying the *Nicotiana tabacum* trnH-psbA Chloroplastic Intergenic Spacer PCR primers were designed to amplify the *Nicotiana tabacum* trnH-psbA chloroplastic intergenic spacer (GenBank accession number FJ493313.1).

SEQ ID NO:1—the *Nicotiana tabacum* trnH-psbA chloroplastic intergenic spacer (GenBank accession number FJ493313.1). The location of amplification primers is underlined.

ACGGGAATTGAACCCGCGCATGGTGGATTCACAATCCACTGCCTTGATCC

ACTTGGCTACATCCGCCCCCTCGCCTACTTACATTCCGTTTTTACATTAT

TTAAATTAGAAAACAAAAGATTCAAGTTCGAATATAGCTCTTCTTTCTTA

TTTCAATGATATTATTATTTCAAAGATAAGAGATATTCAAAGATAAGAGA

TAAGAAGAAGTCAAAATTTGATTTTTTTTTTGGAAAAAAAAAATCAAAAA

GATATAGTAACATTAGCAAGAAGAGAAACAAGTTCTATTTCTACAATTTT

AAACAAATACAAATCAAAATAGAATACTCAATCATGAATAAATGCAAGA

AAATAACCTCTCCTTCTTTTTCTATAATGTAAACAAAAAAGTCTATGTAA

GTAAAATACTAGTAAATAAATAAAAAGAAAAAAAGAAAGGAGCAATAGCA

CCCTCTTGATAGAACAAGAAAATGATTATTGCTCCTTTCTTTTCAAAACC

TCCTATAGACTAGGCCAGGATCTTATCCATTTGTAGATGGAGCTTCGATA

GCAGCTAGGTCTAGAGGGAAGTTGTGAGCATTACGTTCATGCATAAC

SEQ ID NO:2—amplified fragment of the *Nicotiana tabacum* trnH-psbA chloroplast intergenic spacer (GenBank accession number FJ493313.1). The location of amplification primers is underlined.

AGAAAACAAAAGATTCAAGTTCGAATATAGCTCTTCTTTCTTATTTCAAT

GATATTATTATTTCAAAGATAAGAGATATTCAAAGATAAGAGATAAGAAG

AAGTCAAAATTTGATTTTTTTTTTGGAAAAAAAAAATCAAAAGATATAG

TAACATTAGCAAGAAGAGAAACAAGTTCTATTTCTACAATTTTAAACAAA

TACAAATCAAAATAGAATACTCAATCATGAATAAATGCAAGAAAATAAC

CTCTCCTTC

SEQ ID NO:3—forward amplification primer to amplify the *Nicotiana tabacum* trnH-psbA chloroplastic intergenic spacer (GenBank accession number FJ493313.1)

AGAAAACAAAAGATTCAAGTTCG

SEQ ID NO:4—reverse amplification primer to amplify the *Nicotiana tabacum* trnH-psbA chloroplastic intergenic spacer (GenBank accession number FJ493313.1)

GCAAGAAAATAACCTCTCCTTC

PCR is performed in a GeneAmp® PCR System 9700 thermocycler (Applied Biosystems). The reaction mix comprises: TAM (True Allele PCR premix, Applied Biosystems (ThermoFisher)): 6 µL; Forward and reverse primers [10 µM] 0.3 µL; $H_2O$ 2.7 µL and DNA (5-10 ng) 1 µL.

The forward primer is labeled with a fluorescent dye to perform capillary electrophoresis. The primers target the chloroplast DNA in an intergenic spacer region between the trnH and psbA genes.

The following PCR reaction cycles were used: 95° C. for 10 minutes; 35 cycles of 95° C. for 1 minute, 55° C. for 1 minute and 72° C. for 2 minutes; and 72° C. for 7 minutes. After the PCR reaction, a denaturation step of 95° C. for 2 minutes was carried out with: 1 µL of PCR product and 12 µL denaturation mix (1950 µL HiDi Formamide+50 µL GeneScan 400HD ROX size standard). GeneScan 400HD ROX size standard is a product of Applied Biosystems.

After denaturation, fragment electrophoresis was run on an ABI 3130xl Genetic Analyser (Applied Biosystems) using a 36 cm capillary array filled with POP7 polymer (Applied Biosystems).

Analysis of the results is performed using GeneMapper v5.0 software (Applied Biosystems). Two independent and manual reviews of the results are carried out. The *Nicotiana tabacum* trnH-psbA chloroplastic intergenic spacer allows for the differentiation of *Nicotiana tabacum* from the *Nicotiana suaveolens* and *Nicotiana glauca* source of sterility.

The fragment from *Nicotiana tabacum* is expected at about 259 bp.

The fragment from *Nicotiana suaveolens* is expected at about 206 bp.

The fragment from *Nicotiana glauca* is expected at about 238 bp.

Example 2: Analysis of a Tobacco Lot Using the *Nicotiana tabacum* trnH-psbA Chloroplastic Intergenic Spacer

*Nicotiana tabacum* tobacco lots were sourced from tobacco farmers who were provided seed of sterile tobacco hybrids. Polynucleotide was extracted from the tobacco lots and analysed using the methodology described in Example 1.

Testing of the various tobacco lots revealed that at least one of the tobacco lots had a *Nicotiana tabacum* trnH-psbA chloroplastic intergenic spacer size of 206 bp indicating that the tobacco lot contained *Nicotiana suaveolens* cytoplasm and was derived from seed of sterile tobacco hybrids only.

Testing of the various tobacco lots revealed that at least one of the tobacco lots had a *Nicotiana tabacum* trnH-psbA chloroplastic intergenic spacer size of 238 bp indicating that the tobacco lot contained *Nicotiana glauca* cytoplasm and was derived from seed of sterile tobacco hybrids only.

Testing of the various tobacco lots revealed that at least one of the tobacco lots had a *Nicotiana tabacum* trnH-psbA chloroplastic intergenic spacer size of 259 bp indicating that the tobacco lot contained *Nicotiana tabacum* cytoplasm and was derived from seed of fertile tobacco seeds. This result is indicative that sterile tobacco seed was mixed with fertile tobacco material when offered for sale.

Example 3: Method for Amplifying the *Nicotiana tabacum* trnL-trnF Chloroplastic Intergenic Region PCR primers were designed to amplify the *Nicotiana tabacum* trnL-trnF chloroplastic intergenic spacer (GenBank accession number AH003085.2).

SEQ ID NO:5—the *Nicotiana tabacum* trnL-trnF chloroplastic intergenic spacer (GenBank accession number AH003085.2). The location of amplification primers is underlined.

TCAATGGTTCCAGTATAAATGAAAGAAAAAGAAAAAGGAATGACATCACA

ACGAGATCCTAATCTCAAAAAGAAAGGGGGATATGGCGAAATCGGTAGAC

GCTACGGACTTAATTGGATTGAGCCTTGGTATGGAAACTTACTAAGTGAT

CACTTTCAAATTCAGAGAAACCCTGGAATTAACAAAAATGGGCAATCCTG

AGCCAAATCCTGTTTTCCGAAAACAAACAAAGGTTCAGAAAAAAAGGATA

GGTGCAGAGACTCAATGGAAGCTATTCTAACAAATGGAGTTAAAT<u>GCGTT</u>

<u>GGTAGAGGAATCTTT</u>ACATCGAAACTTCAGAAAGAAAAGAATGAAGTGA

AGGATAAACGTATATACATACGTATTGAATACTATATCAAAATCAAATGA

TTAATGATGACCCGAATCTGTATTTTTTCTATAAAAAATAGAAGAATTGG

TGTGAATCGATTCTACATTGAAGAAAGAATCGAATATTCATTGATCAAAC

CATTCACTCCATAGTCTGATAGATCTTTTGAAGAACTGATTAATCGGACG

AGAATAAAGATAGAGTCCCGTTCTACATGTCAATACCGGCAACAATGAAA

TTTATCGTAAGAGGAAAATCCGTCGACTTTAAAAATCGTGAGGGTTCAAG

TCCCTCTATCCCCAAAAAGACTATTTCACTCCCCAACTATTTATCCGACC

CCCTTTCCTTAGCGGTTCCAAATTCCTTATCTTTCTCATTCACTCTATTC

TTTTAGAAAT<u>GGATTTGAGCGTAAATGG</u>CTTTCTCTTATCACAAGTCTTG

TGATATATATGATACACATAGAAATGAACGTCTTTGAGCAAGGAATCCCT

AGTTGAATGATTCCCTATCAATATCATTACTCATACTGAAACTTACAAAG

TCATCTTTTTGAAGATCGAAGAAATTCCCCGGCTTTGAGAAAATTTTTAA

TCTACTTTTGTCCTTGTAATTGACATAGACCCCAGTTCTCTAATAAAATG

AGGATACTACATTGGGAATAGCCGGGATAGCTCAGTTGGTAGAGCAGAGG

ACTGAAAATCCTCGTGTCACCAGTTCAAATCTGGTTCCTGGCACATGATT

AATTTGTATGGGTCTCTCTTCCCTCGAATTAATTTCTAATTAATTGATAT

GAATCAACATACATATTCTTTTAGAGTCTAGATTAGAATAATAGCTTTAT

CCAGTTTGGCGAGATATACCCCATCTATGTTCTAGATGGGTAGAGTTTCT

TAGATAAAGT

SEQ ID NO: 6—amplified fragment of the *Nicotiana tabacum* trnL-trnF chloroplast intergenic spacer (GenBank accession number AH003085.2). The location of amplification primers is underlined.

GCGTTGGTAGAGGAATCTTTACATCGAAACTTCAGAAAGAAAAAGAATGA

AGTGAAGGATAAACGTATATACATACGTATTGAATACTATATCAAAATCA

AATGATTAATGATGACCCGAATCTGTATTTTTTCTATAAAAAATAGAAGA

ATTGGTGTGAATCGATTCTACATTGAAGAAAGAATCGAATATTCATTGAT

CAAACCATTCACTCCATAGTCTGATAGATCTTTTGAAGAACTGATTAATC

GGACGAGAATAAAGATAGAGTCCCGTTCTACATGTCAATACCGGCAACAA

TGAAATTTATCGTAAGAGGAAAATCCGTCGACTTTAAAAATCGTGAGGGT

TCAAGTCCCTCTATCCCCAAAAAGACTATTTCACTCCCCAACTATTTATC

CGACCCCCTTTCCTTAGCGGTTCCAAATTCCTTATCTTTCTCATTCACTC

TATTCTTTTAGAA<u>ATGGATTTGAGCGTAAATGG</u>

SEQ ID NO: 7—forward amplification primer to amplify the *Nicotiana tabacum* trnL-trnF chloroplastic intergenic spacer (GenBank accession number AH003085.2)

GCGTTGGTAGAGGAATCTTT

SEQ ID NO: 8—reverse amplification primer to amplify the *Nicotiana tabacum* trnL-trnF chloroplastic intergenic spacer (GenBank accession number AH003085.2)

ATGGATTTGAGCGTAAATGG

PCR is performed in a GeneAmp® PCR System 9700 thermocycler (Applied Biosystems). The reaction mix comprises: TAM (True Allele PCR premix, Applied Biosystems (ThermoFisher)): 6 µL; Forward and reverse primers [10 µM] 0.3 µL; $H_2O$ 2.7 µL and DNA (5-10 ng) 1 µL.

The forward primer is labeled with a fluorescent dye to perform capillary electrophoresis.

The primers target the chloroplast DNA in an intergenic spacer region between the trnL and trnF genes.

The following PCR reaction cycles were used: 95° C. for 10 minutes; 35 cycles of 95° C. for 1 minute, 55° C. for 1 minute and 72° C. for 2 minutes; and 72° C. for 7 minutes. After the PCR reaction, a denaturation step of 95° C. for 2 minutes was carried out with: 1 µL of PCR product and 12 µL denaturation mix (1950 µL HiDi Formamide+50 µL GeneScan 400HD ROX size standard). GeneScan 400HD ROX size standard is a product of Applied Biosystems.

After denaturation, fragment electrophoresis was run on an ABI 3130xl Genetic Analyser (Applied Biosystems) using a 36 cm capillary array filled with POP7 polymer (Applied Biosystems).

Analysis of the results is performed using GeneMapper v5.0 software (Applied Biosystems). Two independent and manual reviews of the results are carried out. The *Nicotiana tabacum* trnL-trnF chloroplastic intergenic spacer allows for the differentiation of *Nicotiana tabacum* from the *Nicotiana suaveolens* and *Nicotiana glauca* source of sterility.

The fragment from *Nicotiana tabacum* is expected at about 483 bp.

The fragment from *Nicotiana suaveolens* is expected at about 477 bp.

The fragment from *Nicotiana glauca* is expected at about 467 bp.

Example 4: Analysis of a Tobacco Lot Using the *Nicotiana tabacum* trnL-trnF Chloroplastic Intergenic Spacer

*Nicotiana tabacum* tobacco lots were sourced from tobacco farmers who were provided seed of sterile tobacco hybrids. Polynucleotide was extracted from the tobacco lots and analysed using the methodology described in Example 3.

Testing of the various tobacco lots revealed that at least one of the tobacco lots had a *Nicotiana tabacum* trnL-trnF chloroplastic intergenic spacer size of 477 bp indicating that the tobacco lot contained *Nicotiana suaveolens* cytoplasm and was derived from seed of sterile tobacco hybrids only.

Testing of the various tobacco lots revealed that at least one of the tobacco lots had a *Nicotiana tabacum* trnL-trnF chloroplastic intergenic spacer size of 467 bp indicating that the tobacco lot contained *Nicotiana glauca* cytoplasm and was derived from seed of sterile tobacco hybrids only.

Testing of the various tobacco lots revealed that at least one of the tobacco lots had a *Nicotiana tabacum* trnL-trnF chloroplastic intergenic spacer size of 483 bp indicating that the tobacco lot contained *Nicotiana tabacum* cytoplasm and was derived from seed of fertile tobacco seeds. This result is indicative that sterile tobacco seed was mixed with fertile tobacco material when offered for sale.

Example 5—Further Analysis of Tobacco Lots

*Nicotiana tabacum* tobacco lots were sourced from tobacco farmers who were provided seed of sterile tobacco hybrids. Polynucleotide was extracted from the tobacco lots and analysed using the methodology described in Example 1. The fragment from *Nicotiana tabacum* is expected at about 259 bp. The fragment from *Nicotiana suaveolens* is expected at about 206 bp. The fragment from *Nicotiana glauca* is expected at about 238 bp.

The response to testing of a first lot is a single peak in the *N. suaveolens* expected bin (grey bar on the left of the chromatogram) of 206 bp. The pooled samples exhibiting this genotype contain mostly leaves from sterile plants. In this group were also included samples showing a small *N. tabacum* signal at 259 bp (below 30% of the *N. suaveolens* peak height) which can be linked to a low level of contamination in the sample or a low level of adulteration.

The response to testing of a second lot is a single peak in the *N. tabacum* expected bin at 259 bp (grey bar on the right of the chromatogram). The pooled samples exhibiting this genotype contain mostly leaves from fertile plants. In this group were also included samples showing a small *N. suaveolens* signal at 206 bp (below 30% of the *N. tabacum* peak height) which can be linked to a low level of contamination in the sample or a low level of adulteration.

The response to testing of a third lot is a peak in *N. suaveolens* at 206 bp and *N. tabacum* at 259 bp with similar peak heights. The pooled samples exhibiting this genotype contain sterile and fertile material in nearly equivalent proportions.

The response to testing of a fourth lot test is a peak in *N. suaveolens* at 206 bp and *N. tabacum* at 259 bp. However, the peak height in the *N. tabacum* bin represents about 30% or more of the *N. suaveolens* peak height. The pooled samples exhibiting this genotype contain sterile and fertile material in various proportions. The sterile material is more abundant in such pooled sample but there is a non-negligible fraction of fertile plants.

The *N. tabacum* peak height threshold used to classify the samples in this group was chosen arbitrarily. Nevertheless, the level of DNA amplification is high enough to exclude any contamination from the neighbouring samples and sterile crop material adulteration with fertile material.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular, molecular and plant biology or related fields are intended to be within the scope of the following claims.

Sequences (Shown in the 5'-3' Direction)

SEQ ID NO:1 *Nicotiana tabacum* trnH-psbA chloroplastic intergenic spacer nucleotide sequence (GenBank accession number FJ493313.1)

```
ACGGGAATTGAACCCGCGCATGGTGGATTCACAATCCACTGCCTTGATCC

ACTTGGCTACATCCGCCCCCTCGCCTACTTACATTCCGTTTTTACATTAT

TTAAATTAGAAAACAAAAGATTCAAGTTCGAATATAGCTCTTCTTTCTTA

TTTCAATGATATTATTATTTCAAAGATAAGAGATATTCAAAGATAAGAGA

TAAGAAGAAGTCAAAATTTGATTTTTTTTTTGGAAAAAAAAAATCAAAAA

GATATAGTAACATTAGCAAGAAGAGAAACAAGTTCTATTTCTACAATTTT

AAACAAATACAAAATCAAAATAGAATACTCAATCATGAATAAATGCAAGA

AAATAACCTCTCCTTCTTTTTCTATAATGTAAACAAAAAAGTCTATGTAA

GTAAAATACTAGTAAATAAATAAAAAGAAAAAAAGAAAGGAGCAATAGCA

CCCTCTTGATAGAACAAGAAAATGATTATTGCTCCTTTCTTTTCAAAACC

TCCTATAGACTAGGCCAGGATCTTATCCATTTGTAGATGGAGCTTCGATA

GCAGCTAGGTCTAGAGGGAAGTTGTGAGCATTACGTTCATGCATAAC
```

SEQ ID NO:2: Amplified nucleotide sequence of the *Nicotiana tabacum* trnH-psbA chloroplastic intergenic spacer (GenBank accession number FJ493313.1)

```
AGAAAACAAAAGATTCAAGTTCGAATATAGCTCTTCTTTCTTATTTCAAT

GATATTATTATTTCAAAGATAAGAGATATTCAAAGATAAGAGATAAGAAG

AAGTCAAAATTTGATTTTTTTTTTGGAAAAAAAAAATCAAAAAGATATAG

TAACATTAGCAAGAAGAGAAACAAGTTCTATTTCTACAATTTTAAACAAA

TACAAAATCAAAATAGAATACTCAATCATGAATAAATGCAAGAAAATAAC

CTCTCCTTC
```

SEQ ID NO: 3: Forward amplification primer to amplify the *Nicotiana tabacum* trnH-psbA chloroplastic intergenic spacer (GenBank accession number FJ493313.1)

```
AGAAAAAAAAGATTCAAGTTCG
```

SEQ ID NO: 4: Reverse amplification primer to amplify the *Nicotiana tabacum* trnH-psbA chloroplastic intergenic spacer (GenBank accession number FJ493313.1)

GCAAGAAAATAACCTCTCCTTC

SEQ ID NO: 5: *Nicotiana tabacum* trnL-trnF chloroplastic intergenic spacer nucleotide sequence (GenBank accession number AH003085.2)

TCAATGGTTCCAGTATAAATGAAAGAAAAAGAAAAAGGAATGACATCACA

ACGAGATCCTAATCTCAAAAAGAAAGGGGGATATGGCGAAATCGGTAGAC

GCTACGGACTTAATTGGATTGAGCCTTGGTATGGAAACTTACTAAGTGAT

CACTTTCAAATTCAGAGAAACCCTGGAATTAACAAAAATGGGCAATCCTG

AGCCAAATCCTGTTTTCCGAAAACAAACAAAGGTTCAGAAAAAAAGGATA

GGTGCAGAGACTCAATGGAAGCTATTCTAACAAATGGAGTTAAATGCGTT

GGTAGAGGAATCTTTACATCGAAACTTCAGAAAGAAAAAGAATGAAGTGA

AGGATAAACGTATATACATACGTATTGAATACTATATCAAAATCAAATGA

TTAATGATGACCCGAATCTGTATTTTTTCTATAAAAAATAGAAGAATTGG

TGTGAATCGATTCTACATTGAAGAAAGAATCGAATATTCATTGATCAAAC

CATTCACTCCATAGTCTGATAGATCTTTTGAAGAACTGATTAATCGGACG

AGAATAAAGATAGAGTCCCGTTCTACATGTCAATACCGGCAACAATGAAA

TTTATCGTAAGAGGAAAATCCGTCGACTTTAAAAATCGTGAGGGTTCAAG

TCCCTCTATCCCCAAAAAGACTATTTCACTCCCCAACTATTTATCCGACC

CCCTTTCCTTAGCGGTTCCAAATTCCTTATCTTTCTCATTCACTCTATTC

TTTTAGAAATGGATTTGAGCGTAAATGGCTTTCTCTTATCACAAGTCTTG

TGATATATATGATACACATAGAAATGAACGTCTTTGAGCAAGGAATCCCT

AGTTGAATGATTCCCTATCAATATCATTACTCATACTGAAACTTACAAAG

TCATCTTTTTGAAGATCGAAGAAATTCCCCGGCTTTGAGAAAATTTTTAA

TCTACTTTTGTCCTTGTAATTGACATAGACCCCAGTTCTCTAATAAAATG

-continued

AGGATACTACATTGGGAATAGCCGGGATAGCTCAGTTGGTAGAGCAGAGG

ACTGAAAATCCTCGTGTCACCAGTTCAAATCTGGTTCCTGGCACATGATT

AATTTGTATGGGTCTCTCTTCCCTCGAATTAATTTCTAATTAATTGATAT

GAATCAACATACATATTCTTTTAGAGTCTAGATTAGAATAATAGCTTTAT

CCAGTTTGGCGAGATATACCCCATCTATGTTCTAGATGGGTAGAGTTTCT

TAGATAAAGT

SEQ ID NO:6: Amplified nucleotide sequence of the *Nicotiana tabacum* trnL-trnF chloroplastic intergenic spacer (GenBank accession number AH003085.2)

GCGTTGGTAGAGGAATCTTTACATCGAAACTTCAGAAAGAAAAAGAATGA

AGTGAAGGATAAACGTATATACATACGTATTGAATACTATATCAAAATCA

AATGATTAATGATGACCCGAATCTGTATTTTTTCTATAAAAAATAGAAGA

ATTGGTGTGAATCGATTCTACATTGAAGAAAGAATCGAATATTCATTGAT

CAAACCATTCACTCCATAGTCTGATAGATCTTTTGAAGAACTGATTAATC

GGACGAGAATAAAGATAGAGTCCCGTTCTACATGTCAATACCGGCAACAA

TGAAATTTATCGTAAGAGGAAAATCCGTCGACTTTAAAAATCGTGAGGGT

TCAAGTCCCTCTATCCCCAAAAAGACTATTTCACTCCCCAACTATTTATC

CGACCCCCTTTCCTTAGCGGTTCCAAATTCCTTATCTTTCTCATTCACTC

TATTCTTTTAGAAATGGATTTGAGCGTAAATGG

SEQ ID NO: 7: Forward amplification primer to amplify the *Nicotiana tabacum* trnL-trnF chloroplastic intergenic spacer (GenBank accession number AH003085.2)

GCGTTGGTAGAGGAATCTTT

SEQ ID NO: 8: Reverse amplification primer to amplify the *Nicotiana tabacum* chloroplast trnL-trnF intergenic spacer (GenBank accession number AH003085.2)

CCATTTACGCTCAAATCCAT

The invention claimed is:

1. A method for classifying a batch of *Nicotiana tabacum* plant material as either being contaminated or non-contaminated comprising:

(i) providing a sample of polynucleotide from the batch of *Nicotiana tabacum* plant material;

(ii) contacting the sample of polynucleotide with one or more amplification primers to amplify a target polynucleotide sequence associated with sterility, wherein the target polynucleotide sequence associated with sterility is a trnH-psbA chloroplastic intergenic spacer or a trnL-trnF chloroplastic intergenic spacer;

(iii) performing an in vitro polynucleotide amplification reaction on the sample to generate one or more amplification products;

(iv) subjecting the amplification product(s) to a sizing or sequencing process to obtain the size or sequence of the amplification product(s);

(v) digitally comparing the size or sequence of the amplification product(s) size or sequence of a known amplification product(s) from known genetic sources of sterility to determine if the genetic source of sterility is contaminated or non-contaminated, wherein the known genetic source of sterility is from *Nicotiana suaveolens, Nicotiana glauca, Nicotiana bigelovii, Nicotiana plumbaginifolia, Nicotiana megalosiphon* or *Nicotiana undulata*; and (vi) identifying the presence of fertile tobacco material and destroying the *Nicotiana tabacum* plant material.

2. The method according to claim 1, wherein the target polynucleotide sequence associated with sterility is a polynucleotide sequence associated with cytoplasmic male sterility.

3. The method according to claim 1, wherein the presence of a polynucleotide sequence associated with sterility from *Nicotiana suaveolens, Nicotiana glauca, Nicotiana bigelovii, Nicotiana plumbaginifolia, Nicotiana megalosiphon* or *Nicotiana undulata* is indicative that the tobacco plant material is sterile.

4. The method according to claim 1, wherein the batch of tobacco plant material to be classified is *Nicotiana tabacum* plant material and wherein the expected genetic source of sterility is cytoplasmic male sterility from *Nicotiana suaveolens*, and wherein if the genetic source of sterility determined in step (v) corresponds to cytoplasmic male sterility from *Nicotiana suaveolens* then said batch of tobacco plant material is considered to be non-contaminated; or wherein if the genetic source of sterility determined in step (v) does not correspond to cytoplasmic male sterility from *Nicotiana suaveolens* then said batch of tobacco plant material is considered to be contaminated.

5. The method according to claim 1, wherein the batch of tobacco plant material for checking is *Nicotiana tabacum* tobacco plant material and wherein the expected genetic source of sterility is cytoplasmic male sterility from *Nicotiana glauca*, and wherein if the genetic source of sterility determined in step (v) corresponds to cytoplasmic male sterility from *Nicotiana glauca* then said batch of tobacco plant material is considered to be non-contaminated; or wherein if the genetic source of sterility determined in step (v) does not correspond to cytoplasmic male sterility from *Nicotiana glauca* then said batch of tobacco plant material is considered to be contaminated.

6. The method according to claim 1, wherein the tobacco plant material is selected from the group consisting of seedlings, seeds, plants, parts of plants, harvested plant material, cured plant material or a combination of two or more thereof.

7. The method according to claim 1, wherein the size of the amplification product is determined using gel electrophoresis.

8. The method according to claim 7, wherein the size of the amplification product is determined using agarose gel electrophoresis or two dimensional gel electrophoresis or capillary electrophoresis; and/or wherein the sequence of the amplification product is determined using polynucleotide sequencing.

9. The method according to claim 1, wherein the tobacco plant material is sterile hybrid tobacco plant material.

10. The method according to claim 1, wherein the trnH-psbA chloroplastic intergenic spacer comprises or consists of the sequence set forth in SEQ ID NO: 1 or the trnL-trnF chloroplastic intergenic spacer comprises or consists of the sequence set forth in SEQ ID NO: 5.

11. The method of claim 1, wherein the known genetic source of sterility is amplified in step (iii).

12. The method of claim 1, wherein the species from which an amplified polynucleotide is derived can be identified by differences in size or sequence of the amplified polynucleotides.

13. The method of claim 1, wherein the plant material comprises harvested plant material, further comprising identifying the batch of seeds from which the plant material was grown.

14. The method of claim 1, wherein the plant material comprises leaves and stems.

15. A method comprising:

contacting a sample of polynucleotide from a batch of tobacco plant material with two or more amplification primers specific for a polynucleotide sequence associated with sterility, wherein the target polynucleotide sequence associated with sterility is a trnH-psbA chloroplastic intergenic spacer or a trnL-trnF chloroplastic intergenic spacer;

amplifying a polynucleotide comprising the intergenic spacer using the two or more amplification primers to generate an amplification product;

subjecting the amplification product to a sizing or sequencing process to obtain the size or sequence of the amplification product;

identifying the batch of tobacco plant material as having an amplification product(s) size or sequence that does not correspond to a known amplification product(s) from known genetic sources of sterility; and discarding or destroying the identified batch of tobacco plant material.

16. The method according to claim 15, wherein the trnH-psbA chloroplastic intergenic spacer comprises or consists of the sequence set forth in SEQ ID NO: 1 or the trnL-trnF chloroplastic intergenic spacer comprises or consists of the sequence set forth in SEQ ID NO: 5.

17. A method for detecting a genetic source of sterility in a batch of *Nicotiana tabacum* plant material comprising:

(i) contacting a sample of polynucleotide with one or more amplification primers to amplify a target polynucleotide sequence comprising a trnH-psbA chloroplastic intergenic spacer or a trnL-trnF chloroplastic intergenic spacer;

(ii) performing an in vitro polynucleotide amplification reaction on the sample to generate one or more amplification products;

(iii) subjecting the amplification product(s) to a sizing or sequencing process to obtain the size or sequence of the amplification product(s);

(iv) detecting a genetic source of sterility based on the size or sequence of the amplification product(s), wherein the genetic source of sterility is from *Nicotiana suaveolens, Nicotiana glauca, Nicotiana bigelovii, Nicotiana plumbaginifolia, Nicotiana megalosiphon* or *Nicotiana undulata*, and (v) destroying the batch of *Nicotiana tabacum* plant material.

18. The method according to claim 17, wherein the trnH-psbA chloroplastic intergenic spacer comprises or consists of the sequence set forth in SEQ ID NO: 1 or the trnL-trnF chloroplastic intergenic spacer comprises or consists of the sequence set forth in SEQ ID NO: 5.

* * * * *

SEQUENCE LISTING

<160> NUMBER OF SEQ ID NOS: 8

<210> SEQ ID NO 1
<211> LENGTH: 597
<212> TYPE: DNA
<213> ORGANISM: Nicotiana tabacum

<400> SEQUENCE: 1

```
acgggaattg aacccgcgca tggtggattc acaatccact gccttgatcc acttggctac      60
atccgccccc tcgcctactt acattccgtt tttacattat ttaaattaga aaacaaaaga     120
ttcaagttcg aatatagctc ttctttctta tttcaatgat attattattt caaagataag     180
agatattcaa agataagaga taagaagaag tcaaaatttg atttttttttt tggaaaaaaa     240 aaatcaaaaa gatatagtaa cattagcaag aagagaaaca agttctattt ctacaatttt     300
aaacaaatac aaaatcaaaa tagaatactc aatcatgaat aaatgcaaga aaataacctc     360
```

```
tccttctttt tctataatgt aaacaaaaaa gtctatgtaa gtaaaatact agtaaataaa       420
taaaaagaaa aaaagaaagg agcaatagca ccctcttgat agaacaagaa aatgattatt       480
gctcctttct tttcaaaacc tcctatagac taggccagga tcttatccat ttgtagatgg       540
agcttcgata gcagctaggt ctagagggaa gttgtgagca ttacgttcat gcataac        597

<210> SEQ ID NO 2
<211> LENGTH: 259
<212> TYPE: DNA
<213> ORGANISM: Nicotiana tabacum

<400> SEQUENCE: 2
agaaaacaaa agattcaagt tcgaatatag ctcttctttc ttatttcaat gatattatta        60
tttcaaagat aagagatatt caaagataag agataagaag aagtcaaaat ttgatttttt       120
ttttggaaaa aaaaaatcaa aaagatatag taacattagc aagaagagaa acaagttcta       180
tttctacaat tttaaacaaa tacaaaatca aaatagaata ctcaatcatg aataaatgca       240
agaaaataac ctctccttc                                                    259

<210> SEQ ID NO 3
<211> LENGTH: 23
<212> TYPE: DNA
<213> ORGANISM: Artificial Sequence
<220> FEATURE:
<223> OTHER INFORMATION: Forward amplification primer to amplify the
      Nicotiana tabacum trnH-psbA chloroplastic intergenic spacer

<400> SEQUENCE: 3
agaaaacaaa agattcaagt tcg                                                 23

<210> SEQ ID NO 4
<211> LENGTH: 22
<212> TYPE: DNA
<213> ORGANISM: Artificial Sequence
<220> FEATURE:
<223> OTHER INFORMATION: Reverse amplification primer to amplify the
      Nicotiana tabacum trnH-psbA chloroplastic intergenic spacer
      (GenBank accession number FJ493313.1)

<400> SEQUENCE: 4
gcaagaaaat aacctctcct tc                                                  22

<210> SEQ ID NO 5
<211> LENGTH: 1260
<212> TYPE: DNA
<213> ORGANISM: Nicotiana tabacum

<400> SEQUENCE: 5
tcaatggttc cagtataaat gaaagaaaaa gaaaaaggaa tgacatcaca acgagatcct        60
aatctcaaaa agaaaggggg atatggcgaa atcggtagac gctacggact taattggatt       120
gagccttggt atggaaactt actaagtgat cactttcaaa ttcagagaaa ccctggaatt       180
aacaaaaatg ggcaatcctg agccaaatcc tgttttccga aaacaaacaa aggttcagaa       240
aaaaaggata ggtgcagaga ctcaatggaa gctattctaa caaatggagt taaatgcgtt       300
ggtagaggaa tctttacatc gaaacttcag aaagaaaaag aatgaagtga aggataaacg       360
tatatacata cgtattgaat actatatcaa aatcaaatga ttaatgatga cccgaatctg       420 tatttttct ataaaaaata gaagaattgg tgtgaatcga ttctacattg aagaaagaat       480
cgaatattca ttgatcaaac cattcactcc atagtctgat agatcttttg aagaactgat       540
```

-continued

```
taatcggacg agaataaaga tagagtcccg ttctacatgt caataccggc aacaatgaaa      600
tttatcgtaa gaggaaaatc cgtcgacttt aaaaatcgtg agggttcaag tccctctatc      660
cccaaaaaga ctatttcact ccccaactat ttatccgacc cccttttcctt agcggttcca     720 aattccttat ctttctcatt cactctattc ttttagaaat ggatttgagc gtaaatggct      780
ttctcttatc acaagtcttg tgatatatat gatacacata gaaatgaacg tctttgagca      840
aggaatccct agttgaatga ttccctatca atatcattac tcatactgaa acttacaaag      900
tcatcttttt gaagatcgaa gaaattcccc ggctttgaga aaatttttaa tctacttttg      960
tccttgtaat tgacatagac cccagttctc taataaaatg aggatactac attgggaata      1020
gccgggatag ctcagttggt agagcagagg actgaaaatc ctcgtgtcac cagttcaaat     1080
ctggttcctg gcacatgatt aatttgtatg ggtctctctt ccctcgaatt aatttctaat     1140
taattgatat gaatcaacat acatattctt ttagagtcta gattagaata atagctttat     1200
ccagtttggc gagatatacc ccatctatgt tctagatggg tagagtttct tagataaagt     1260
```

```
<210> SEQ ID NO 6
<211> LENGTH: 483
<212> TYPE: DNA
<213> ORGANISM: Nicotiana tabacum

<400> SEQUENCE: 6
gcgttggtag aggaatcttt acatcgaaac ttcagaaaga aaaagaatga agtgaaggat       60
aaacgtatat acatacgtat tgaatactat atcaaaatca aatgattaat gatgacccga      120
atctgtattt tttctataaa aaatagaaga attggtgtga atcgattcta cattgaagaa      180
agaatcgaat attcattgat caaaccattc actccatagt ctgatagatc ttttgaagaa      240
ctgattaatc ggacgagaat aaagatagag tcccgttcta catgtcaata ccggcaacaa      300
tgaaatttat cgtaagagga aaatccgtcg actttaaaaa tcgtgagggt tcaagtccct      360
ctatccccaa aaagactatt tcactcccca actatttatc cgaccccctt tccttagcgg      420
ttccaaattc cttatctttc tcattcactc tattcttttta gaaatggatt tgagcgtaaa      480
tgg                                                                     483
```

```
<210> SEQ ID NO 7
<211> LENGTH: 20
<212> TYPE: DNA
<213> ORGANISM: Artificial Sequence
<220> FEATURE:
<223> OTHER INFORMATION: Forward amplification primer to amplify the
      Nicotiana tabacum trnL-trnF chloroplastic intergenic spacer

<400> SEQUENCE: 7
gcgttggtag aggaatcttt                                                     20
```

```
<210> SEQ ID NO 8
<211> LENGTH: 20
<212> TYPE: DNA
<213> ORGANISM: Artificial Sequence
<220> FEATURE:
<223> OTHER INFORMATION: Reverse amplification primer to amplify the
      Nicotiana tabacum chloroplast trnL-trnF intergenic spacer

<400> SEQUENCE: 8
ccatttacgc tcaaatccat                                                     20
```